US007931906B2

(12) United States Patent
Lee et al.

(10) Patent No.: US 7,931,906 B2
(45) Date of Patent: Apr. 26, 2011

(54) VERO CELL-BASED INFLUENZA VIRUS STRAINS AND VACCINES

(75) Inventors: Min-Shi Lee, Taipei (TW); Yu-Shuan Chen, Kaohsiung County (TW); Yu-Fen Tseng, Taipei County (TW); Pele Choi-Sing Chong, Miaoli County (TW)

(73) Assignee: National Health Research Institutes, Miaoli County (TW)

( * ) Notice: Subject to any disclaimer, the term of this patent is extended or adjusted under 35 U.S.C. 154(b) by 138 days.

(21) Appl. No.: 12/204,826

(22) Filed: Sep. 5, 2008

(65) Prior Publication Data

US 2009/0074804 A1 Mar. 19, 2009

Related U.S. Application Data

(60) Provisional application No. 60/970,270, filed on Sep. 6, 2007.

(51) Int. Cl.
*A61K 39/145* (2006.01)

(52) U.S. Cl. .................................. 424/209.1; 424/186.1

(58) Field of Classification Search ........................ None
See application file for complete search history.

(56) References Cited

OTHER PUBLICATIONS

Nicolson et al., Vaccine, 2005, 23:2943-2952.*

* cited by examiner

*Primary Examiner* — Stacy B Chen
(74) *Attorney, Agent, or Firm* — Hsiu-Ming Saunders; Intellectual Property Connections, Inc.

(57) ABSTRACT

The present invention relates to isolated influenza virus strains suitable for increased vaccine production for mammals. The influenza virus strains contain at least one modified influenza protein that results in increased production of the influenza virus from a mammalian host cell, such as a vero cell. The present invention also relates to the vaccines produced from the influenza virus strains. The present invention further relates to isolated modified influenza proteins and isolated nucleic acid molecules that encode for the modified influenza proteins.

11 Claims, 10 Drawing Sheets

C

B

A

```
                          Position*
A   (NT)        1   583-584  1257  1737
    16          GTC----TT----T----A-------
    15          GTC----TT----T----A-------
    NIBRG-14    GTC----AA----C----G-------

                          Position*
B   (AA)        1      195
    16          V------L------------------
    15          V------L------------------
    NIBRG-14    V------K------------------
```

| (NT) | Position* |
|---|---|
| | 1 1076 |
| 16 | GAA--------A------- |
| 15 | GAA--------A------- |
| NIBRG-14 | GAA--------C------- |

B

| (AA) | Position* |
|---|---|
| | 1 359 |
| 16 | E-----------Y---- |
| 15 | E-----------Y---- |
| NIBRG-14 | E-----------S---- |

| (NT) | 1 | 763 | 921 | 1229 | 1337 | 1413 |
|---|---|---|---|---|---|---|
| 16 | CAC | G | A | T | T | T |
| 15 | CAC | A | C | C | C | C |
| NIBRG-14 | CAC | A | C | C | C | C |

Position*

B

| (AA) | 1 | 255 | 410 | 446 |
|---|---|---|---|---|
| 16 | H | D | F | F |
| 15 | H | N | S | S |
| NIBRG-14 | H | N | S | S |

Position*

A

| (NT) | Position* | | |
|---|---|---|---|
| | 1 | 694 | 706 |
| 16 | TAT | T | T |
| 15 | TAT | C | C |
| NIBRG-14 | TAT | C | C |

B

| (AA) | Position* | |
|---|---|---|
| | 1 | 236 |
| 16 | Y | F |
| 15 | Y | L |
| NIBRG-14 | Y | L |

A

| (NT) | 1 | 895 | 1054 | 1394 | 1482 |
|---|---|---|---|---|---|
| 16 | CAAA | C | C | C | A |
| 15 | CAAA | T | T | T | G |
| NIBRG-14 | CAAA | T | T | T | A |

B

| (AA) | 1 | 465 | 494 |
|---|---|---|---|
| 16 | K | H | E |
| 15 | K | Y | G |
| NIBRG-14

VERO CELL-BASED INFLUENZA VIRUS STRAINS AND VACCINES

CROSS REFERENCE TO RELATED APPLICATIONS

This application claims the benefit of U.S. Provisional Application No. 60/970,270, filed Sep. 6, 2007, which is herein incorporated by reference in its entirety.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 362355SequenceListing.txt, a creation date of Sep. 4, 2008, and a size of 55 KB. The sequence listing filed via EFS-Web is part of the specification and is hereby incorporated in its entirety by reference herein.

FIELD OF THE INVENTION

The present invention relates to an influenza virus stain. In particular, the present invention relates to an influenza A virus strain suitable for increased production of an influenza A virus vaccine from a mammalian host cell, and the vaccine produced therefrom.

BACKGROUND OF THE INVENTION

Influenza viruses, particularly types A and B viruses, have been associated with major outbreaks of influenza, and are a serious cause of morbidity and mortality of animals. Infection with type B influenza is usually milder than type A. Influenza A viruses are hosted by birds, but may infect several species of mammals. All known subtypes of influenza A are endemic in birds. Birds have the greatest number and range of influenza strains. The influenza virus strains have been and are undergoing antigenic drift, probably driven by selective antibody pressure in the populations of humans infected, leading to seasonal epidemics in several geographical regions. Recently, it was found that highly pathogenic avian influenza A viruses of the H5N1 subtype were circulating in eastern Asia. Some strains of the human H5N1 viruses were isolated and studied. In 2005, some H5N1 isolates lacking the polybasic cleavage site in the hemagglutinin gene were produced by reverse genetics in anticipation of the possible need to vaccinate humans. See *Emerging Infectious Disease* (2005) 11(10):1515-1521.

An influenza virus is an RNA virus of the Orthomyxoviridae family and comprises a segment negative RNA genome, which codes for about 10 influenza proteins. The 10 influenza proteins include RNA-directed RNA polymerase proteins (PB2, PB1 and PA), nucleoprotein (NP), neuraminidase (NA), hemagglutinin (HA, which after enzymatic cleavage is made up of the association of subunits HA1 and HA2), the matrix proteins (M1 and M2) and the non-structural proteins (NS1 and NS2) (Krug et al. (1989) in *The Influenza Viruses* (R. M. Krug, ed.), Plenum Press (New York) pages 89-152).

For the past several decades, fertilized chicken eggs have been used as a host system to replicate influenza viruses for use in vaccine production. African green monkey kidney (Vero) cells and Madin-Darby canine kidney (MDCK) cells have been widely used for manufacturing seasonal influenza vaccines (Audrey et al. (2004) *Expert Opin. Biol. Ther.* 4(5): 709-17 and Ghendon et al. (2005) *Vaccine* 23(38):4678-84).

A current influenza H5N1 vaccine strain, NIBRG-14, was provided by the National Institute of Biological and Serum Control, the United of Kingdom (UK NIBSC), which is a reassortant virus containing HA and NA gene segments of A/Vietnam/1194/2004 (H5N1) virus and the other six internal gene segments of A/PuertoRico/8/1934 (H1N1) virus. It was found that this vaccine strain could grow efficiently in chicken embryonated eggs and MDCK cells but not in Vero cells (Govorkova et al. (1999) *Dev. Biol. Stand.* 98:39-51). However, in the case of a pandemic influenza, chicken eggs would be insufficient and suboptimal for influenza vaccine production, and there are concerns over the tumorogenic potential of MDCK cells.

Therefore, there is a need for an influenza virus strain that is able to grow efficiently in Vero cells and suitable for increased production of an influenza vaccine from a mammalian host cell. The present invention satisfies this need.

BRIEF SUMMARY OF THE INVENTION

In one aspect, embodiments of the present invention relate to an isolated influenza A virus strain that is able to grow efficiently in a mammalian host cell and is suitable for increased production of an influenza vaccine from the mammalian host cell. The isolated influenza A virus strain comprises at least one gene that encodes at least one modified influenza protein, as described herein below, wherein expression of the at least one modified influenza protein results in an increased production of the influenza virus from a mammalian host cell.

In another aspect, embodiments of the present invention relate to an influenza vaccine. The vaccine comprises an influenza A virus strain according to an embodiment of the invention and a pharmaceutically acceptable carrier. Embodiments of the present invention also relate to a method of preparing the influenza vaccine.

Isolated nucleic acid molecules that encode a modified influenza protein and the isolated modified influenza proteins are also provided. Other aspects, features and advantages of the invention will be apparent from the following disclosure, including the detailed description of the invention and the appended claims.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For purposes of illustrating the invention, there are shown in the drawings embodiments which are presently preferred. It should be understood, however, that the invention is not limited to the precise embodiments shown.

FIG. 5 illustrates the sequence alignment analysis of the amino acid (AA) sequences of the influenza virus PB 1 protein (FIG. 5B) and their corresponding nucleotide (NT) sequences (FIG. 5A) among the strains Vero-15, Vero-16 and NIBRG-14;

FIG. 6 illustrates the sequence alignment analysis of the amino acid (AA) sequences of the influenza virus PB2 protein (FIG. 6B) and their corresponding nucleotide (NT) sequences (FIG. 6A) among the strains Vero-15, Vero-16 and NIBRG-14;

DETAILED DESCRIPTION OF THE INVENTION

Figure 1:
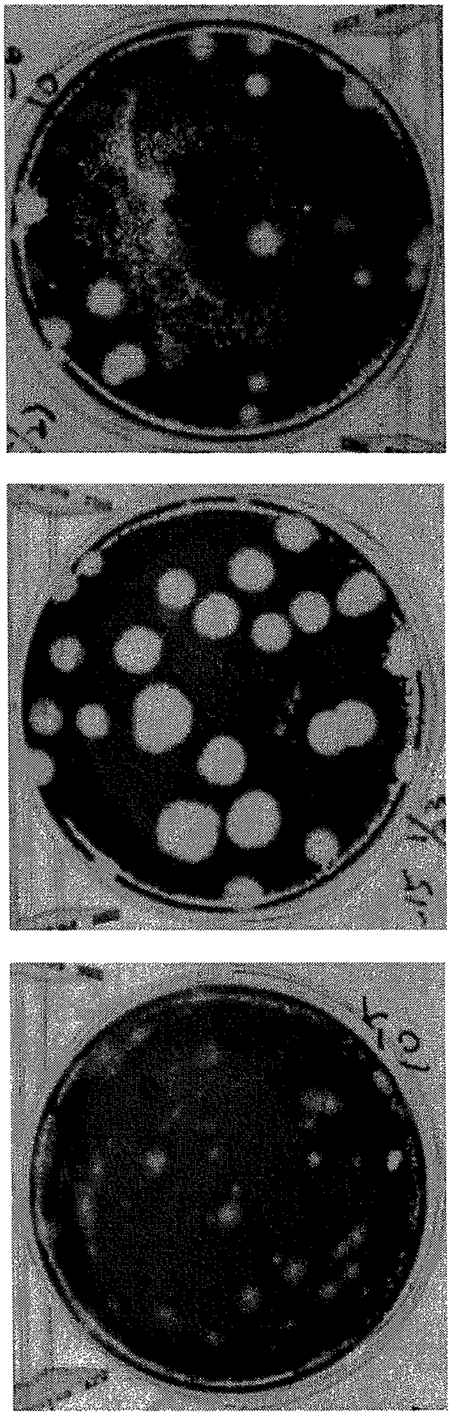
FIG. 1 shows an image of the plaque morphology of the strain NIBRG-14 (FIG. 1A) and the influenza virus strains Vero-15 (FIG. 1B) and Vero-16 (FIG. 1C) after 6 days (for the strain NIBRG-14) and 3 days (for the strains Vero-15 and Vero-16) post-infection in Vero cells.

The present invention relates to high-growth influenza virus strains, which are suitable for replicating in mammalian host cells. In accordance with embodiments of the present invention, a H5N1 vaccine virus strain, such as the strain NIBRG-14, was subjected to serial passages in mammalian primary cells, such as Vero cells, and the high-growth strains were selected, isolated, and characterized.

Unless defined otherwise, all technical and scientific terms used herein have the same meaning as commonly understood to one of ordinary skill in the art to which this invention pertains. In this application, certain terms are used frequently, which shall have the meanings as set forth in the specification. It must be noted that as used herein and in the appended claims, the singular forms "a," "an," and "the" include plural referents unless the context clearly dictates otherwise.

As used herein, a "reassortant" virus refers to a virus which contains gene segments originated from two or more different virus strains. The reassortant virus will share properties of its parental lineages. For example, a reassortant virus can have gene segments encoding antigenic proteins from a virus strain of interest (e.g., HA and NA genes) and have gene segments encoding other viral proteins, such as the polymerase complex (e.g., PB2, PB1 and PA genes) and other viral proteins (e.g., non-glycoprotein genes, including M genes, NS genes, and NP genes) from viruses adapted for growth in culture (or attenuated viruses). The reassortant virus thus carries the desired antigenic characteristics in a background or master strain that permits efficient production in a host cell. Such a reassortant virus is a desirable "virus seed" for production of virions for vaccine production. In one embodiment of the present invention, the reassortant virus includes strain NIBRG-14 and any modified strain of NIBRG-14, such as the Vero-15 or Vero-16 strains, described herein below.

As used herein, the term "modified strain" means a strain of a first virus strain obtained by serial passages and/or selection of the first virus and its progenies in a mammalian host cell. In one embodiment of the present invention, the modified strain has increased virus production from the mammalian host cell compared to that of the first virus strain.

As used herein, the term "influenza protein" refers to any polypeptide or protein encoded by an influenza gene.

As used herein, a "gene" is a segment of nucleic acid molecule involved in producing a peptide, polypeptide, or protein, and the mRNA encoding such protein species, including the coding region, non-coding regions preceding ("5'UTR") and following ("3'UTR") the coding region. A "gene" may also include intervening non-coding sequences ("introns") between individual coding segments ("exons"). A gene may further include a regulatory sequence, which controls the expression of the gene. A "regulatory sequence" can include promoters, enhancers and other expression control elements such as polyadenylation signals, ribosome binding site (for bacterial expression), and/or, an operator. A "promoter" means a regulatory sequence that is involved in the binding of RNA polymerase to initiate transcription of a gene. Promoters are often upstream ("5' to") the transcription initiation site of the gene. An "enhancer" means a regulatory sequence that can regulate the expression of a gene in a distance- and orientation-dependent fashion. A "coding region" refers to the portion of a gene that encodes amino acids and the start and stop signals for the translation of the corresponding polypeptide via triplet-base codons.

As used herein, an "influenza gene" can be any gene originally isolated and/or identified from an influenza virus. The influenza gene can be a gene originally isolated and/or identified from any influenza virus. In particular embodiments of the present invention, the influenza gene is originally isolated and/or identified from an influenza A virus.

As used herein, the term "modified influenza protein" refers to a protein that includes one or more modifications to the amino acid sequence of an unmodified or reference influenza protein. The modification includes, for example, an insertion, substitution, or deletion of one or more amino acid residues of an unmodified or reference influenza protein. Therefore, the modified influenza protein can have at least one modified amino acid residue and/or codon occupying an identified location of an unmodified or reference protein.

For the purpose of simplicity and clarity, a modification in a modified influenza protein is identified by its corresponding position in an influenza protein from a particular reference influenza virus strain, i.e., influenza NIBRG-14. However, such identification is not meant to limit the modified influenza protein to a modified influenza NIBRG-14 protein only. The modified influenza protein can be a modified influenza protein from any influenza virus that contains the modification at a position corresponding to that in the influenza NIBRG-14 protein. One of skill in the art can identify such corresponding positions in other influenza viruses utilizing standard techniques.

As used herein, the term "an amino acid substitution" refers to the presence of the amino acid at an identified location in the amino acid sequence of a modified protein. The amino acid substitution occurs relative to any other amino acid that could have occupied that location of an unmodified or reference protein. The modified protein comprising the amino acid substitution can also include other modifications.

As used herein, a "modified influenza PB1 protein comprising a leucine residue at the position corresponding to position 195 of SEQ ID NO:1" refers to a modified influenza PB1 protein that has a leucine residue at the position corresponding to position 195 of SEQ ID NO:1. The modified influenza PB1 protein is not limited to a modified PB1 protein from influenza NIBRG-14 that has the substitution of lysine to leucine at position 195 of SEQ ID NO:1. The leucine residue occurs relative to any other amino acid residues that could have occupied that location of an unmodified or reference PB1 protein. The modified influenza PB1 protein can be a modified PB1 protein from influenza A viruses other than NIBRG-14 so long as the modified PB1 protein has a leucine residue at the position corresponding to position 195 of SEQ ID NO:1. The modified influenza PB1 protein can also include modifications in addition to the specified leucine residue. As used herein, "position 195 of SEQ ID NO:1" refers to the $195^{th}$ amino acid residue of SEQ ID NO:1 counting from the N-terminal end of SEQ ID NO:1. In view of the present disclosure, the position in PB1 proteins from other influenza viruses A corresponding to position 195 of SEQ ID NO:1 can be readily identified by the skilled artisan using methods known in the art, such as sequence alignment analysis. Similar interpretations apply to other modified influenza proteins, such as PB2, NP, M, PA and NS, that are herein described in a similar manner.

As used herein, the term "modified influenza PB1 protein" refers to a protein that includes one or more modifications to the amino acid sequence of an unmodified or reference influenza PB1 protein. An influenza PB1 protein, encoded by an influenza PB1 gene, is a subunit of an influenza RNA-dependent RNA polymerase. The influenza PB1 gene is located on segment 2 of the segmented negative strand influenza A genome. Examples of influenza PB1 genes include, but are not limited to, the PB1 gene of influenza A virus, e.g., having the nucleotide sequence of SEQ ID NO:2 isolated from NIBRG-14 virus; having the nucleotide sequence set forth in GenBank Accession No. NC__0049111.1 isolated from influenza A/Hong Kong/1073/99(H9N2); having the nucleotide sequence set forth in GenBank Accession No. NC__007372.1 isolated from influenza A/New York/392/2004(H3N2); having the nucleotide sequence set forth in GenBank Accession No. NC__007375.1 isolated from influenza A/Korea/426/68 (H2N2); having the nucleotide sequence set forth in GenBank Accession No. NC__002021.1 isolated from influenza A/Puerto Rico/8/34(H1N1); or having the nucleotide sequence set forth in GenBank Accession No. NC__007358.1 isolated from influenza A/Goose/Guangdong/1/96(H5N1).

As used herein, the term "modified influenza PB2 protein" refers to a protein that includes one or more modifications to the amino acid sequence of an unmodified or reference influenza PB2 protein. An influenza PB2 protein, encoded by an influenza PB2 gene, is also a subunit of an influenza RNA-dependent RNA polymerase. The influenza PB2 gene is located on segment 1 of the segmented negative strand influenza A genome. Examples of influenza PB2 genes include, but are not limited to, the PB2 gene of influenza A virus, e.g., having the nucleotide sequence set forth in SEQ ID NO:4 isolated from NIBRG-14 virus; having the nucleotide sequence set forth in GenBank Accession No. NC__004910.1 isolated from influenza A/Hong Kong/1073/99(H9N2); having the nucleotide sequence set forth in GenBank Accession No. NC__007373.1 isolated from influenza A/New York/392/2004(H3N2); having the nucleotide sequence set forth in GenBank Accession No. NC__007378.1 isolated from influenza A/Korea/426/68(H2N2); having the nucleotide sequence set forth in GenBank Accession No. NC__002023.1 isolated from influenza A/Puerto Rico/8/34(H1N1); or having the nucleotide sequence set forth in GenBank Accession No. NC__007357.1 isolated from influenza A/Goose/Guangdong/1/96(H5N1).

As used herein, the term "modified influenza NP protein" refers to a protein that includes one or more modifications to the amino acid sequence of an unmodified or reference influenza NP protein. An influenza NP protein, encoded by an influenza NP gene, is an influenza nucleoprotein. The influenza NP gene is located on segment 5 of the segmented negative strand influenza A genome. Examples of influenza NP genes include, but are not limited to, the NP gene of influenza A virus, e.g., having the nucleotide sequence set forth in SEQ ID NO:6 isolated from NIBRG-14 virus; having the nucleotide sequence set forth in GenBank Accession No. NC__004905.2 isolated from influenza A/Hong Kong/1073/99(H9N2); having the nucleotide sequence set forth in GenBank Accession No. NC__007369.1 isolated from influenza A/New York/392/2004(H3N2); having the nucleotide sequence set forth in GenBank GeneID: 3655111 isolated from influenza A/Korea/426/68(H2N2); having the nucleotide sequence set forth in GenBank Accession No. NC__002019.1 isolated from influenza A/Puerto Rico/8/34 (H1N1); or having the nucleotide sequence set forth in GenBank Accession No. NC__007360.1 isolated from influenza A/Goose/Guangdong/1/96(H5N1).

As used herein, the term "modified influenza M protein" refers to a protein that includes one or more modifications to the amino acid sequence of an unmodified or reference influenza M protein. An influenza M protein is the larger protein of the two influenza matrix proteins encoded by an influenza M gene. The influenza M gene is located on segment 7 of the segmented negative strand influenza A genome. Examples of influenza M genes include, but are not limited to, the M gene of influenza A virus, e.g., having the nucleotide sequence set forth in SEQ ID NO:8 isolated from NIBRG-14 virus; having the nucleotide sequence set forth in GenBank Accession No. NC__004907.1 isolated from influenza A/Hong Kong/1073/99(H9N2); having the nucleotide sequence set forth in GenBank Accession No. NC__007367.1 isolated from influenza A/New York/392/2004(H3N2); having the nucleotide sequence set forth in GenBank Accession No. NC__007377.1 isolated from influenza A/Korea/426/68(H2N2); having the nucleotide sequence set forth in GenBank Accession No. NC__002016.1 isolated from influenza A/Puerto Rico/8/34(H1N1); or having the nucleotide sequence set forth in GenBank Accession No. NC__007363.1 isolated from influenza A/Goose/Guangdong/1/96(H5N1).

As used herein, the term "modified influenza PA protein" refers to a protein that includes one or more modifications to the amino acid sequence of an unmodified or reference influenza PA protein. An influenza PA protein, encoded by an influenza PA gene, is an influenza polymerase PA. The influenza PA gene is located on segment 3 of the segmented negative strand influenza A genome. Examples of influenza PA genes include, but are not limited to, the PA gene of influenza A virus, e.g., having the nucleotide sequence set forth in SEQ ID NO:10 isolated from NIBRG-14 virus; having the nucleotide sequence set forth in GenBank Accession No. NC_004912.1 isolated from influenza A/Hong Kong/1073/99(H9N2); having the nucleotide sequence set forth in GenBank Accession No. NC_007371.1 isolated from influenza A/New York/392/2004(H3N2); having the nucleotide sequence set forth in GenBank Accession No. NC_007376.1 isolated from influenza A/Korea/426/68(H2N2), having the nucleotide sequence set forth in GenBank Accession No. NC_002022.1 isolated from influenza A/Puerto Rico/8/34 (H1N1); or having GenBank Accession No. NC_007359.1 isolated from influenza A/Goose/Guangdong/1/96(H5N1).

As used herein, the term "modified influenza NS protein" refers to a protein that includes one or more modifications to the amino acid sequence of an unmodified or reference influenza NS protein. An influenza NS protein, encoded by an influenza NS gene, is an influenza non-structural protein. The influenza NS gene is located on segment 8 of the segmented negative strand influenza A genome. Examples of influenza NS genes include, but are not limited to, the NS gene of influenza A virus, e.g., having the nucleotide sequence set forth in SEQ ID NO:12 isolated from NIBRG-14 virus; having the nucleotide sequence set forth in GenBank Accession No. NC_004906.1 isolated from influenza A/Hong Kong/1073/99(H9N2), having the nucleotide sequence set forth in GenBank Accession No. NC_007370.1 isolated from influenza A/New York/392/2004(H3N2); having the nucleotide sequence set forth in GenBank Gene ID 3655110 isolated from influenza A/Korea/426/68(H2N2); having the nucleotide sequence set forth in GenBank Accession No. NC_002020.1 isolated from influenza A/Puerto Rico/8/34 (H1N1); or having the nucleotide sequence set forth in GenBank Accession No. NC_007364.1 isolated from influenza A/Goose/Guangdong/1/96(H5N1).

As used herein, the term "nucleotide sequence" refers to the arrangement of either deoxyribonucleotide or ribonucleotide residues in a polymer in either single- or double-stranded form. Nucleic acid sequences can be composed of natural nucleotides of the following bases: thymidine, adenine, cytosine, guanine, and uracil; abbreviated T, A, C, G, and U, respectively, and/or synthetic analogs of the natural nucleotides.

As used herein, an "isolated" nucleic acid molecule is one that is substantially separated from at least one of the other nucleic acid molecules present in the natural source of the nucleic acid, or is substantially free of at least one of the chemical precursors or other chemicals when the nucleic acid molecule is chemically synthesized. An "isolated" nucleic acid molecule can also be, for example, a nucleic acid molecule that is substantially free of at least one of the nucleotide sequences that naturally flank the nucleic acid molecule at its 5' and 3' ends in the genomic DNA of the organism from which the nucleic acid is derived. A nucleic acid molecule is "substantially separated from" or "substantially free of" other nucleic acid molecule(s) or other chemical(s) in preparations of the nucleic acid molecule when there is less than about 30%, 20%, 10%, or 5% or less, and preferably less than 1%, (by dry weight) of the other nucleic acid molecule(s) or the other chemical(s) (also referred to herein as a "contaminating nucleic acid molecule" or a "contaminating chemical").

Isolated nucleic acid molecules include, without limitation, separate nucleic acid molecules (e.g., cDNA or genomic DNA fragments produced by PCR or restriction endonuclease treatment) independent of other sequences, as well as nucleic acid molecules that are incorporated into a vector, an autonomously replicating plasmid, a virus (e.g., a retrovirus, adenovirus, or herpes virus), or into the genomic DNA of a prokaryote or eukaryote. In addition, an isolated nucleic acid molecule can include a nucleic acid molecule that is part of a hybrid or fusion nucleic acid molecule. An isolated nucleic acid molecule can be a nucleic acid sequence that is: (i) amplified in vitro by, for example, polymerase chain reaction (PCR); (ii) synthesized by, for example, chemical synthesis; (iii) recombinantly produced by cloning; or (iv) purified, as by cleavage and electrophoretic or chromatographic separation.

As used herein, the terms "polypeptide" and "protein" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide" and "protein" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, ubiquitinated forms, etc. Modifications also include intra-molecular crosslinking, and covalent attachment to various moieties such as lipids, flavin, biotin, polyethylene glycol or derivatives thereof, etc. In addition, modifications may also include cyclization, branching and crosslinking. Further, amino acids other than the conventional twenty amino acids encoded by the codons of genes may also be included in a polypeptide.

An "isolated protein" or "isolated polypeptide" is one that is substantially separated from at least one of the other proteins present in the natural source of the protein, or is substantially free of at least one of the chemical precursors or other chemicals when the protein is chemically synthesized. A protein is "substantially separated from" or "substantially free of" other protein(s) or other chemical(s) in preparations of the protein when there is less than about 30%, 20%, 10%, or 5% or less, and preferably less than 1%, (by dry weight) of the other protein(s) or the other chemical(s) (also referred to herein as a "contaminating protein" or a "contaminating chemical").

Isolated proteins can have several different physical forms. The isolated protein can exist as a full-length nascent or unprocessed polypeptide, or as a partially processed polypeptide or as a combination of processed polypeptides. The full-length nascent polypeptide can be postranslationally modified by specific proteolytic cleavage events that result in the formation of fragments of the full-length nascent polypeptide. A fragment, or physical association of fragments can have the biological activity associated with the full-length polypeptide; however, the degree of biological activity associated with individual fragments can vary.

An isolated polypeptide or isolated protein can be a non-naturally occurring polypeptide. For example, an isolated polypeptide can be a "hybrid polypeptide." An isolated polypeptide can also be a polypeptide derived from a naturally occurring polypeptide by additions or deletions or substitutions of amino acids. An isolated polypeptide can also be a "purified polypeptide" which is used herein to mean a specified polypeptide in a substantially homogeneous preparation substantially free of other cellular components, other polypeptides, viral materials, or culture medium, or when the polypeptide is chemically synthesized, chemical precursors or by-products associated with the chemical synthesis. A "purified polypeptide" can be obtained from natural or recombinant host cells by standard purification techniques, or by chemical synthesis, as will be apparent to skilled artisans.

An "isolated influenza virus strain" or "isolated influenza virus" is one virus that is substantially separated from at least one of the other viruses present in the natural environment of the virus, or is substantially free of a parental virus strain when the virus is derived, modified, or otherwise originated from the parental virus strain. A virus is "substantially separated from" or "substantially free of" other virus(es) when there is less than about 30%, 20%, 10%, or 5% or less, and preferably less than 1%, (by dry weight) of the other virus(es) (also referred to herein as a "contaminating virus").

In one aspect, the present invention thus relates to an isolated influenza virus strain that produces high titer virus in mammalian cells. Embodiments of the present invention relate to an isolated influenza virus strain that comprises at least one gene that encodes at least one modified influenza protein, and the expression of the at least one modified protein results in an increased production of the influenza virus from a mammalian host cell. In accordance with examples of the invention, the host cells may be selected from the group consisting of mammalian cells suitable for preparing vaccine for use in humans. As a specific example of the invention, the mammalian cells may be Vero cells approved and certified according to the World Health Organization (WHO) requirements for vaccine production. The at least one modified influenza protein includes, but is not limited to, a protein selected from group consisting of:

(a) a modified influenza PB1 protein comprising a leucine residue at the position corresponding to position 195 of SEQ ID NO:1;

(b) a modified influenza PB2 protein comprising a tyrosine residue at the position corresponding to position 359 of SEQ ID NO:3;

(c) a modified influenza NP protein comprising an aspartic acid residue and two phenylalanine residues at the positions corresponding to positions 255, 410 and 446 of SEQ ID NO:5, respectively;

(d) a modified influenza M protein comprising a phenylalanine residue at the position corresponding to position 236 of SEQ ID NO:7;

(e) a modified influenza PA protein comprising a histidine residue or a glycine residue at the position corresponding to position 465 or 494 of SEQ ID NO:9, respectively;

(f) a modified influenza NS protein comprising (i) two proline residues at the positions corresponding to positions 90 and 110 of SEQ ID NO:11; or (ii) a stop codon at the position corresponding to position 122 of SEQ ID NO:11.

One particular example of an embodiment of the invention relates to an influenza virus strain Vero-15. The isolated and modified influenza virus strain Vero-15 comprises a PB1 gene encoding a protein comprising an amino acid sequence of SEQ ID NO:1 with a leucine substitution at position 195 of SEQ ID NO:1, a PB2 gene encoding a protein comprising an amino acid sequence of SEQ ID NO:3 with a tyrosine substitution at position 359 of SEQ ID NO:3, a PA gene encoding a protein having an amino acid sequence of SEQ ID NO:9 with a glycine substitution at position 494 of SEQ ID NO:9, and an NS gene encoding a protein having an amino acid sequence of SEQ ID NO:11 with two proline substitutions at positions 90 and 110 of SEQ ID NO:11, respectively. The influenza virus strain Vero-15 further comprises an HA gene encoding a protein comprising the amino acid sequence of SEQ ID NO:13, an NA gene encoding a protein comprising the amino acid sequence of SEQ ID NO:15, an NP gene encoding a protein comprising the amino acid sequence of SEQ ID NO:5, and an M gene encoding a protein comprising the amino acid sequence of SEQ ID NO:7.

In terms of nucleotides, the influenza virus strain Vero-15 comprises a PB1 gene comprising a nucleotide sequence of SEQ ID NO:2 with three thymine substitutions at positions 583, 584 and 1257 and an adenine substitution at position 1737 of SEQ ID NO:2; a PB2 gene comprising a nucleotide sequence of SEQ ID NO:4 with an adenine substitution at position 1077 of SEQ ID NO:4; a PA gene comprising a nucleotide sequence of SEQ ID NO:10 with a guanine substitution at position 1482 of SEQ ID NO:10; and an NS gene comprising a nucleotide sequence of SEQ ID NO:12 with three cytosine substitutions at positions 271, 331 and 335 of SEQ ID NO:12, respectively. The influenza virus strain Vero-15 further comprises a HA gene comprising the nucleotide sequence of SEQ ID NO:14, and an NA gene comprising the nucleotide sequence of SEQ ID NO:16. The influenza virus strain Vero-15 also further comprises an NP gene comprising a nucleotide sequence of SEQ ID NO:6 and an M gene comprising a nucleotide sequence of SEQ ID NO:8.

By comparing the nucleotide sequence of the strain Vero-15 with that of the strain NIBRG-14, there are 1 to 4 nucleotide differences in the 4 segments PB2, PB1, PA and NS, even though the nucleotide sequences in the HA, NA, NP and M segments are not different from those of the strain NIBRG-14. The detailed comparisons are shown in Table 1 and FIGS. 5 through 10.

In another example of and embodiment of the invention, a modified influenza virus strain Vero-16 is provided. The influenza virus strain Vero-16 comprises a PB1 gene encoding a protein comprising an amino acid sequence of SEQ ID NO:1 with a leucine substitution at position 195 of SEQ ID NO:1; a PB2 gene encoding a protein comprising an amino acid sequence of SEQ ID NO:3 with a tyrosine substitution at position 359 of SEQ ID NO:3; an NP gene encoding a protein comprising an amino acid sequence of SEQ ID NO:5 with an aspartic acid substitution and two phenylalanine substitutions at positions 255, 410 and 446 of SEQ ID NO:5, respectively; an M gene encoding a protein comprising an amino acid sequence of SEQ ID NO:7 with a phenylalanine substitution at position 236 of SEQ ID NO:7; a PA gene encoding a protein comprising an amino acid sequence of SEQ ID NO:9 with a histidine substitution at position 465 of SEQ ID NO:9; and an NS gene encoding a protein comprising an amino acid sequence of SEQ ID NO:11 with a stop codon substitution at position 122 of SEQ ID NO:11. The influenza virus strain further comprises a HA gene encoding a protein comprising the amino acid sequence of SEQ ID NO:13 and an NA gene encoding a protein comprising the amino acid sequence of SEQ ID NO:15.

In terms of nucleotides, the influenza virus strain Vero-16 comprises a PB1 gene comprising a nucleotide sequence of SEQ ID NO:2 with three thymine substitutions at positions 583, 584, and 1257 and an adenine substitution at position 1737 of SEQ ID NO:2, respectively; a PB2 gene comprising a nucleotide sequence of SEQ ID NO:4 with an adenine substitution at position 1077 of SEQ ID NO:4; an NP gene comprising a nucleotide sequence of SEQ ID NO:6 with four thymine substitutions at positions 921, 1229, 1337 and 1413 of SEQ ID NO:6, respectively; an M gene comprising a nucleotide sequence of SEQ ID NO:8 with two thymine substitutions at positions 694 and 706 of SEQ ID NO:8, respectively; a PA gene comprising a nucleotide sequence of SEQ ID NO:10 with three cytosine substitutions at positions 895, 1054, and 1394 of SEQ ID NO:10, respectively; and an NS gene comprising a nucleotide sequence of SEQ ID NO:12 with a nucleotide deletion at position 365 of SEQ ID NO:12. The influenza virus strain Vero-16 further comprises an HA gene comprising the nucleotide sequence of SEQ ID NO:14 and an NA gene comprising the nucleotide sequence of SEQ ID NO:16.

By comparing the nucleotide sequence of the strain Vero-16 with that of the strain NIBRG-14, there are 1 to 5 nucleotide differences in the 6 segments PB2, PB1, PA, NS, NP and M, even though the nucleotide sequences in the HA and NA segments are not different from those of the strain NIBRG-14. The detailed comparisons are shown in Table 1 and FIGS. 5 through 10.

Accordingly, the present invention also provides an improved method of producing an influenza vaccine (e.g., an H5N1 vaccine). The improvement comprises using a modified seed virus for producing the vaccine. The modified seed virus comprises at least one modification selected from the group consisting of a modified PB1 gene encoding a protein having a leucine residue at the position corresponding to position 195 of SEQ ID NO:1; a modified PB2 gene encoding a protein having a tyrosine residue at the position corresponding to position 359 of SEQ ID NO:3; a modified NP gene encoding a protein having an aspartic acid residue and two phenylalanine residues at positions corresponding to positions 255, 410, and 446 of SEQ ID NO:5, respectively; a modified M gene encoding a protein having a phenylalanine residue at the position corresponding to position 236 of SEQ ID NO:7; a modified PA gene encoding a protein having a histidine residue or a glycine residue at the position corresponding to position 465 or 494 of SEQ ID NO:9, respectively; and a modified NS gene encoding a protein having two proline residues at the positions corresponding to positions 90 and 110 or a stop codon at the position corresponding to position 122 of SEQ ID NO:11, respectively.

In terms of nucleotides, the modified seed influenza virus strain used for producing an influenza vaccine (e.g., an H5N1 vaccine) comprises at least one modification selected from the group consisting of a modified PB1 gene having three thymine residues at positions 583, 584, and 1257 and an adenine residue at position 1737 of SEQ ID NO:2, respectively; a modified PB2 gene having an adenine residue at position 1077 of SEQ ID NO:4; a modified NP gene having a guanine residue at position 763 and four thymine residues at positions 921, 1229, 1337 and 1413 of SEQ ID NO:6, respectively; a modified M gene having two thymine residues at positions 694 and 706 of SEQ ID NO:8, respectively; a modified PA gene having a guanine residue at position 1482 or three cytosine residues at positions 895, 1054, and 1394 of SEQ ID NO:10, respectively; and a modified NS gene having three cytosine residues at positions 271, 331 and 335 or a nucleotide deletion at position 365 of SEQ ID NO:12, respectively.

Another aspect of the present invention relates to an influenza vaccine comprising at least one of the modified influenza virus strains according to embodiments of the invention, or any combination thereof. In accordance with the invention, the influenza virus strains can be attenuated or inactivated, formulated and administered, according to known methods, as a vaccine to induce an immune response in a mammal in view of the present disclosure. Any standard methods which are well known in the art may be used for determining the antigenicity. The vaccine compositions may include a pharmaceutically acceptable carrier. The phrase “pharmaceutically acceptable carrier” refers to molecular entities and compositions that are physiologically tolerable and do not typically produce an allergic or similar untoward reaction, such as gastric upset, dizziness and the like, when administered to a human. The term “carrier” refers to a diluent, adjuvant, saline solution, and an aqueous dextrose and glycerol solution are employed as a carrier, particularly for an injectable solution. The term “adjuvant” refers to a compound or mixture that enhances the immune response to an antigen.

The vaccine of the present invention may be administered topically, parenterally, transmucosally, e.g., orally, nasally, or rectally, or transdermally. Administration that is parenteral, e.g., via intravenous injection, also includes, but is not limited to, intra-arteriolar, intramuscular, intradermal, subcutaneous, intraperitoneal, intraventricular, and intracranial.

Aspects of the present invention also relate to isolated nucleic acid molecules encoding modified influenza proteins and methods related to their production, isolation, and use. Such an isolated nucleic acid molecule can be used, for example, for the construction of influenza viruses that grow more efficiently in a host cell. It is discovered in the present invention that an influenza virus grows more efficiently in a host cell when the virus contains one or more of the modified influenza proteins described herein. Therefore, to obtain a fast growing influenza virus, nucleic acid molecules encoding the modified influenza proteins can be combined with virus genes of interest via reassortment or other types of genetic manipulation. Such genetic methods would be known to a person skilled in the art in view of the present invention. The isolated nucleic acid molecule can also be used for the recombinant production of a modified influenza protein encoded by the nucleic acid molecule.

The present invention further relates to isolated modified influenza proteins and methods related to their production, isolation and use. Such isolated proteins can be used, for example, for the production of antibodies to the modified proteins.

The invention will now be described in further detail with reference to the following specific, non-limiting examples:

EXPERIMENTAL EXAMPLES

Example 1

Modification of NIBRG-14 in Vero Cells

The influenza vaccine strain NIBRG-14 was provided by the National Institute from Biological Standards and Control (NIBSC), the United Kingdom (UK), and propagated in embryonated chickens' eggs. The WHO vaccine-approved Vero cells were obtained from the Taiwan Center for Disease Control, and were grown in M199 medium (Gibco BRL, USA) containing 5% fetal bovine serum (FBS) within passages 135 to 150. After 3 serial passages of the Vero cells in T75 flasks supplemented with 2 μg/ml of L-(tosylamido-2-phenyl)ethyl chloromethyl ketone (TPCK) trypsin (Sigma, St. Louis, Mo.), the cell culture supernatant was first inoculated into 96-well plates, followed by 2 rounds of plaque purification in 6-well plates. For each of the clones, virus accumulation was estimated by visual determination of the cytopathic effect and HA titration. The HA titrations were conducted in 96-well microplates using turkey red blood cells (RBC) following the standard technique. The virus infectious titers were measured using the 50% tissue culture infectious doses (TCID50) assay based on cytopathic effect or plaque assay based on plaque forming unit (PFU) in Vero cells supplemented with 4 μg/ml of TPCK-trypsin (WHO manual on animal influenza diagnosis and surveillance, WHO (2002)).

In the measurement of virus growth curves in Vero cells, the Influenza H5N1 vaccine virus clones were grown in T75 flasks supplemented with 4 μg/ml of TPCK-trypsin and the supernatant was harvested at day 1 to 5 post-infection for measuring HA titer and infectious virus titer. Two Vero-adapted influenza H5N1 vaccine virus strains with a high growth were selected and named as Vero-15 and Vero-16, respectively. In the measurement of the virus growth curves in Vero cells of the strain NIBRG-14, the multiplicities of infection (MOI) were $10^{-1}$, $10^{-2}$, and $10^{-3}$ TCID50/cells. For the Vero-adapted strains Vero-15 and Vero-16, the MOI's were $10^{-3}$ and $10^{-4}$.

Figure 2:
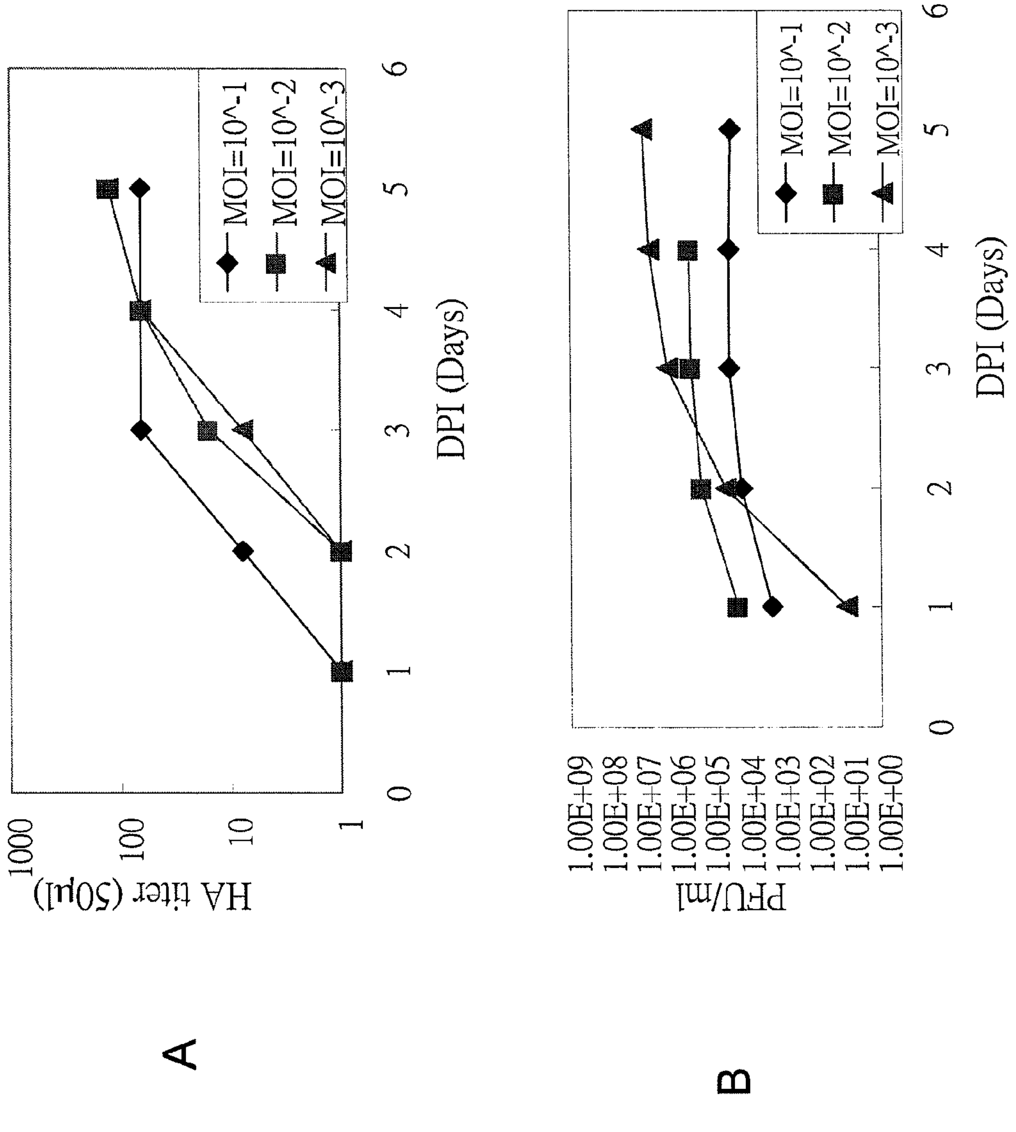
FIG. 2 shows the growth curve in terms of HA titer (50 μl) (FIG. 2A) or infectious virus titer (PFU/ml) (FIG. 2B) of the strain NIBRG-14 in Vero cells as a function of days post-infection (DPI)
Figure 3:
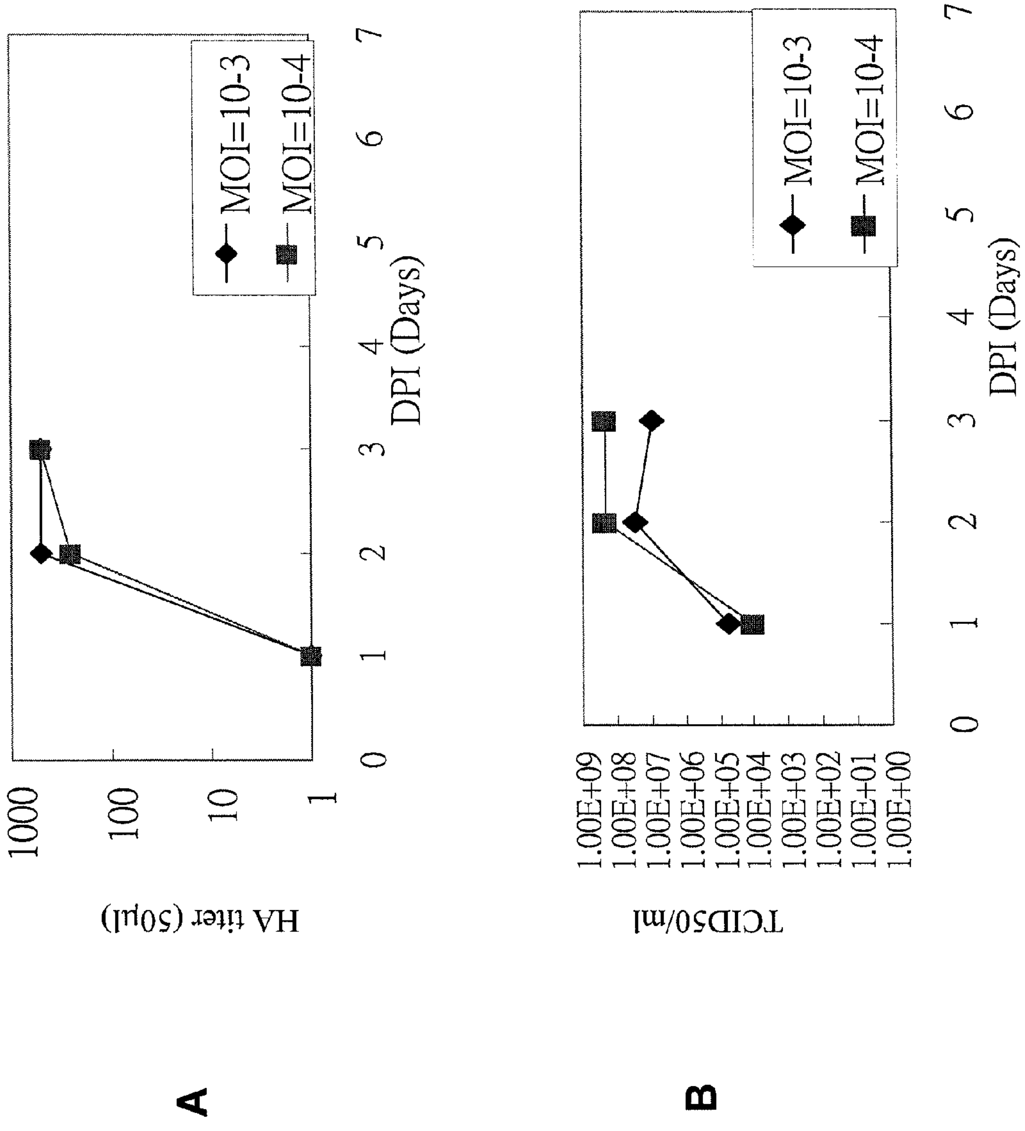
FIG. 3 shows the growth curve in teems of HA titer (50 μl) (FIG. 3A) or infectious virus titer (TCID50/ml) (FIG. 3B) of the strain Vero-15 in Vero cells as a function of days post-infection (DPI)
Figure 4:
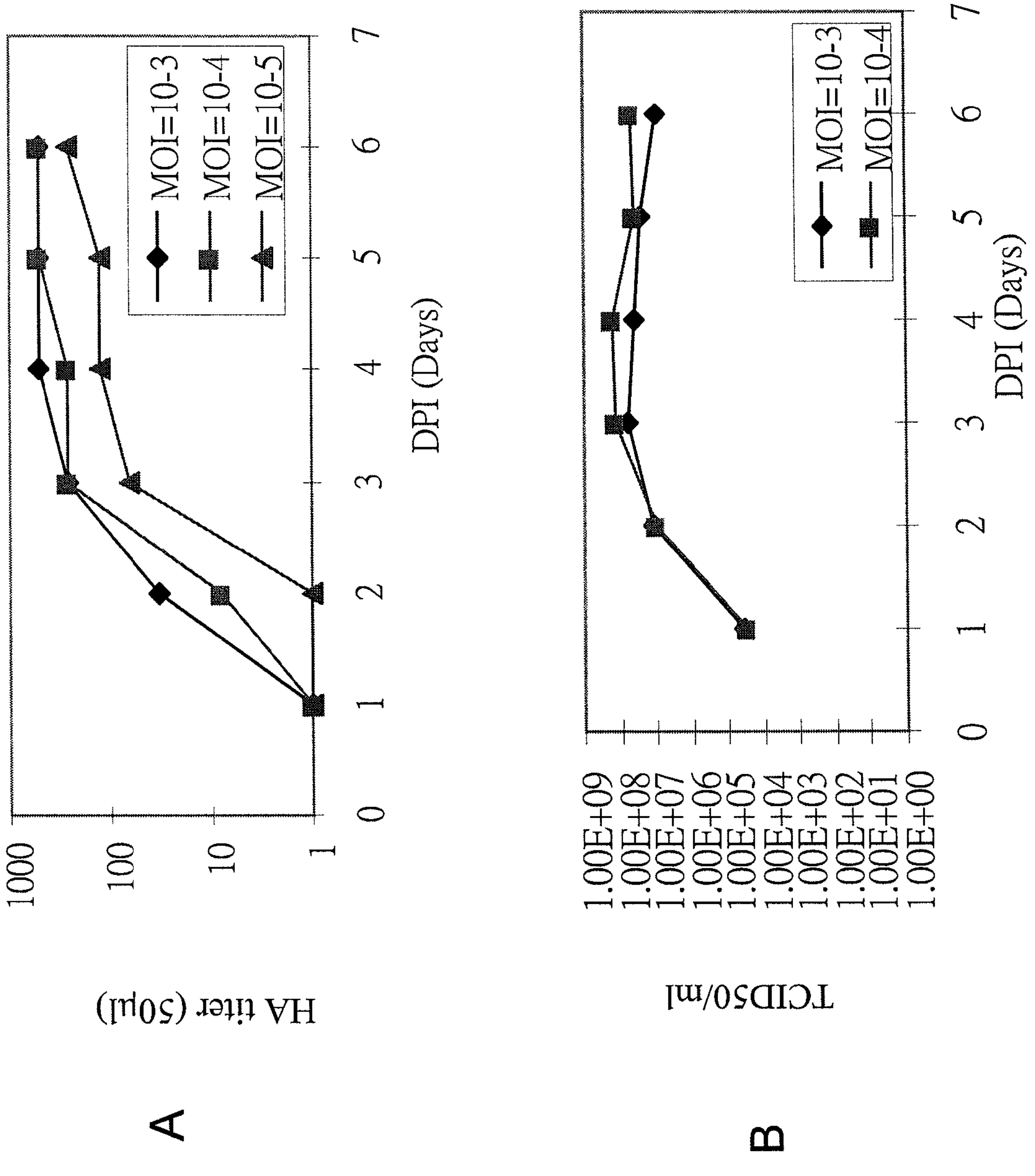
FIG. 4 shows the growth curve in terms of HA titer (50 μl) (FIG. 4A) or infectious virus titer (TCID50/ml) (FIG. 4B) of the strain Vero-16 in Vero cells as a function of days post-infection (DPI)
Figure 7:
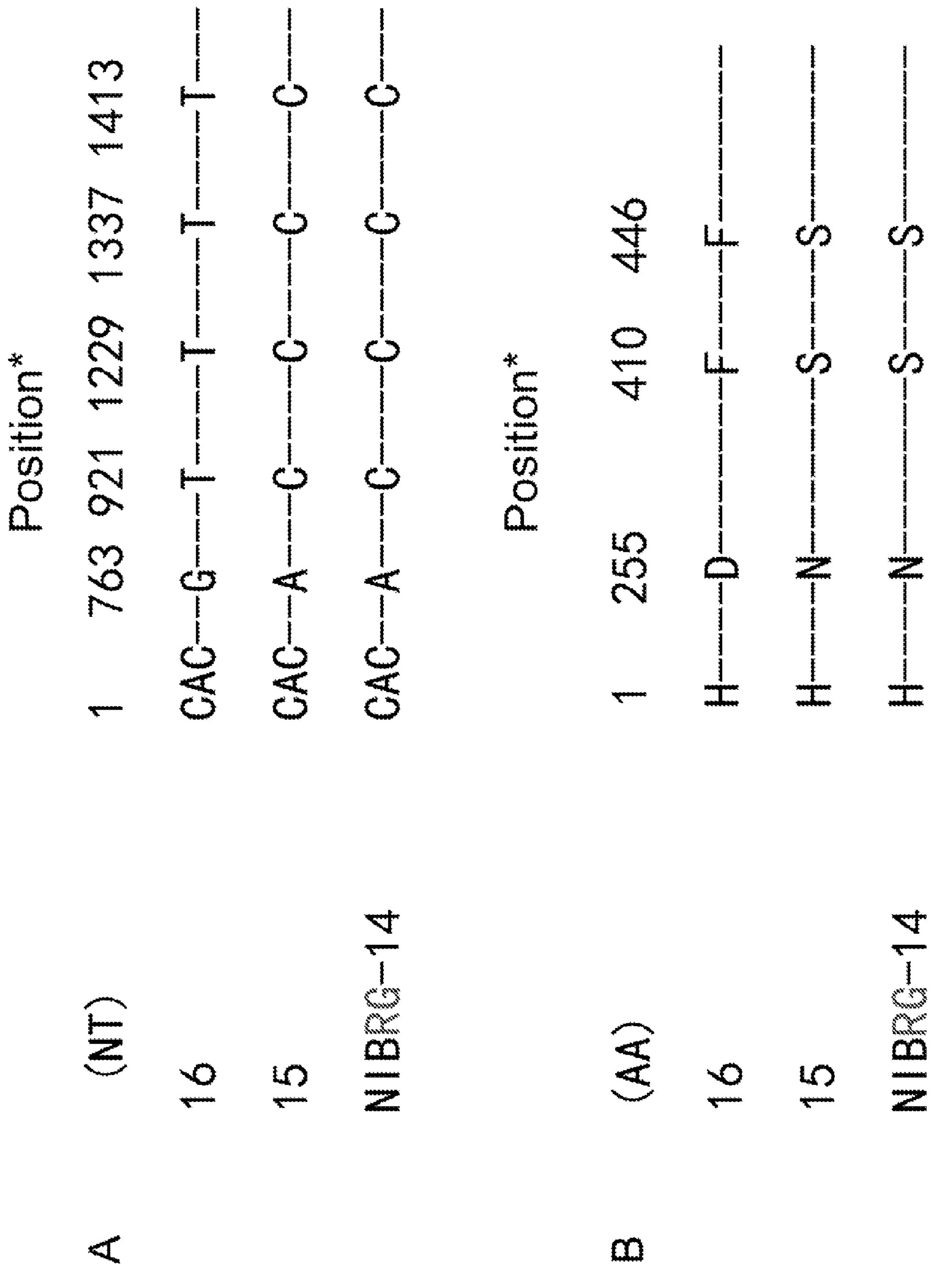
FIG. 7 illustrates the sequence alignment analysis of the amino acid (AA) sequences of the influenza virus NP protein (FIG. 7B) and their corresponding nucleotide (NT) sequences (FIG. 7A) among the strains Vero-15, Vero-16 and NIBRG-14.
Figure 8:
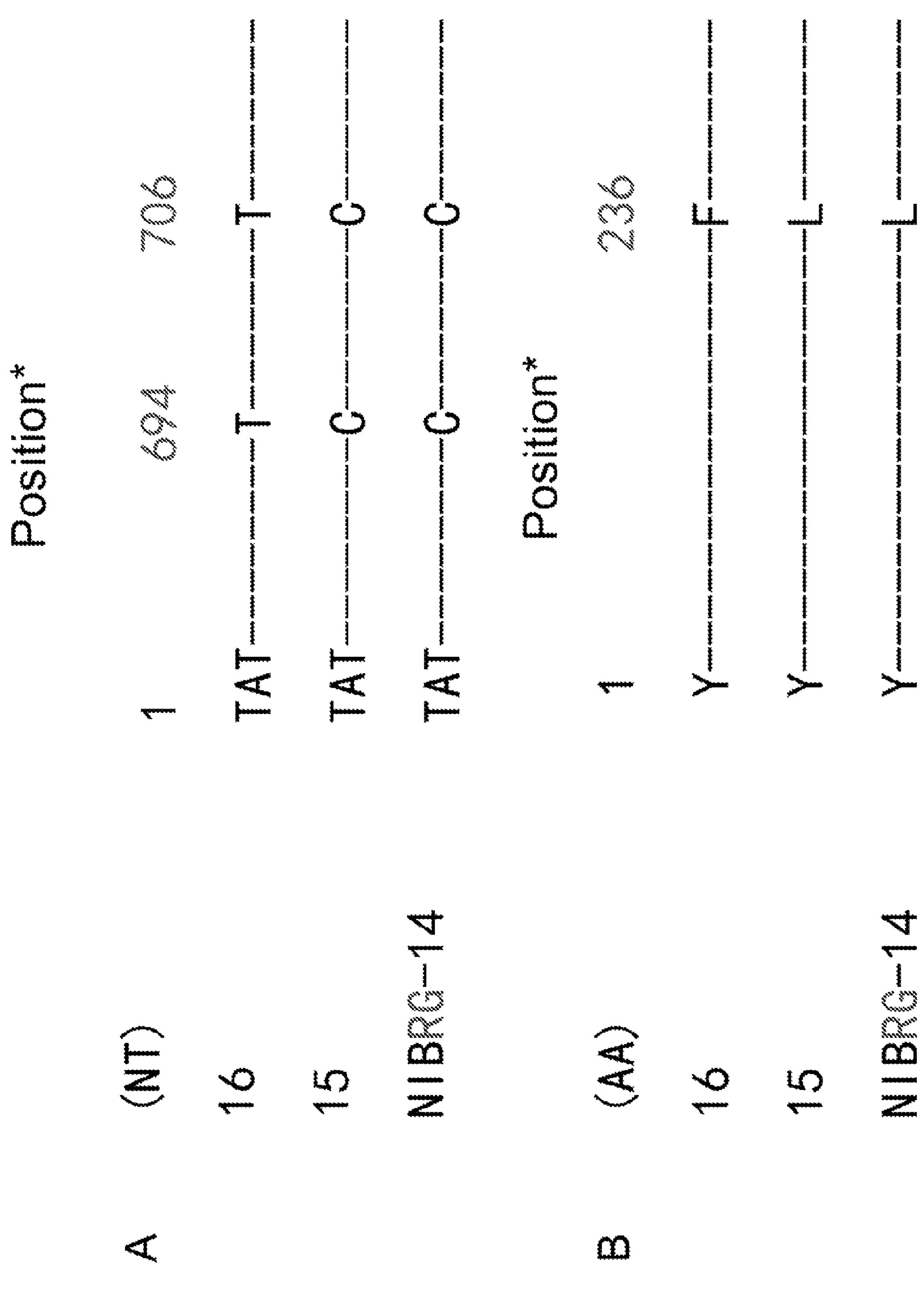
FIG. 8 illustrates the sequence alignment analysis of the amino acid (AA) sequences of the influenza virus M protein (FIG. 8B) and their corresponding nucleotide (NT) sequences (FIG. 8A) among the strains Vero-15, Vero-16 and NIBRG-14.
Figure 9:
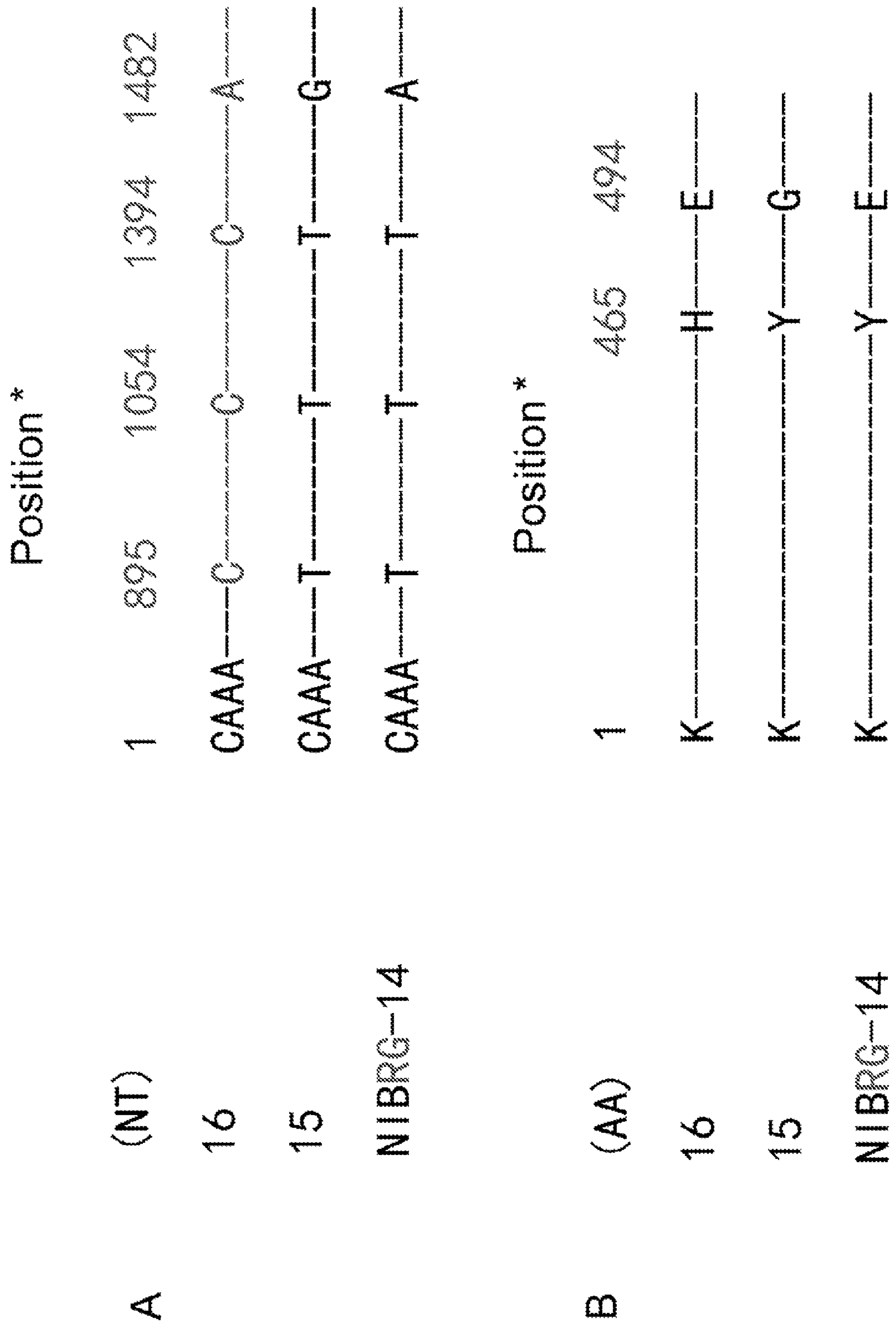
FIG. 9 illustrates the sequence alignment analysis of the amino acid (AA) sequences of the influenza virus PA protein (FIG. 9B) and their corresponding nucleotide (NT) sequences (FIG. 9A) among the strains Vero-15, Vero-16 and NIBRG-14.
Figure 10:
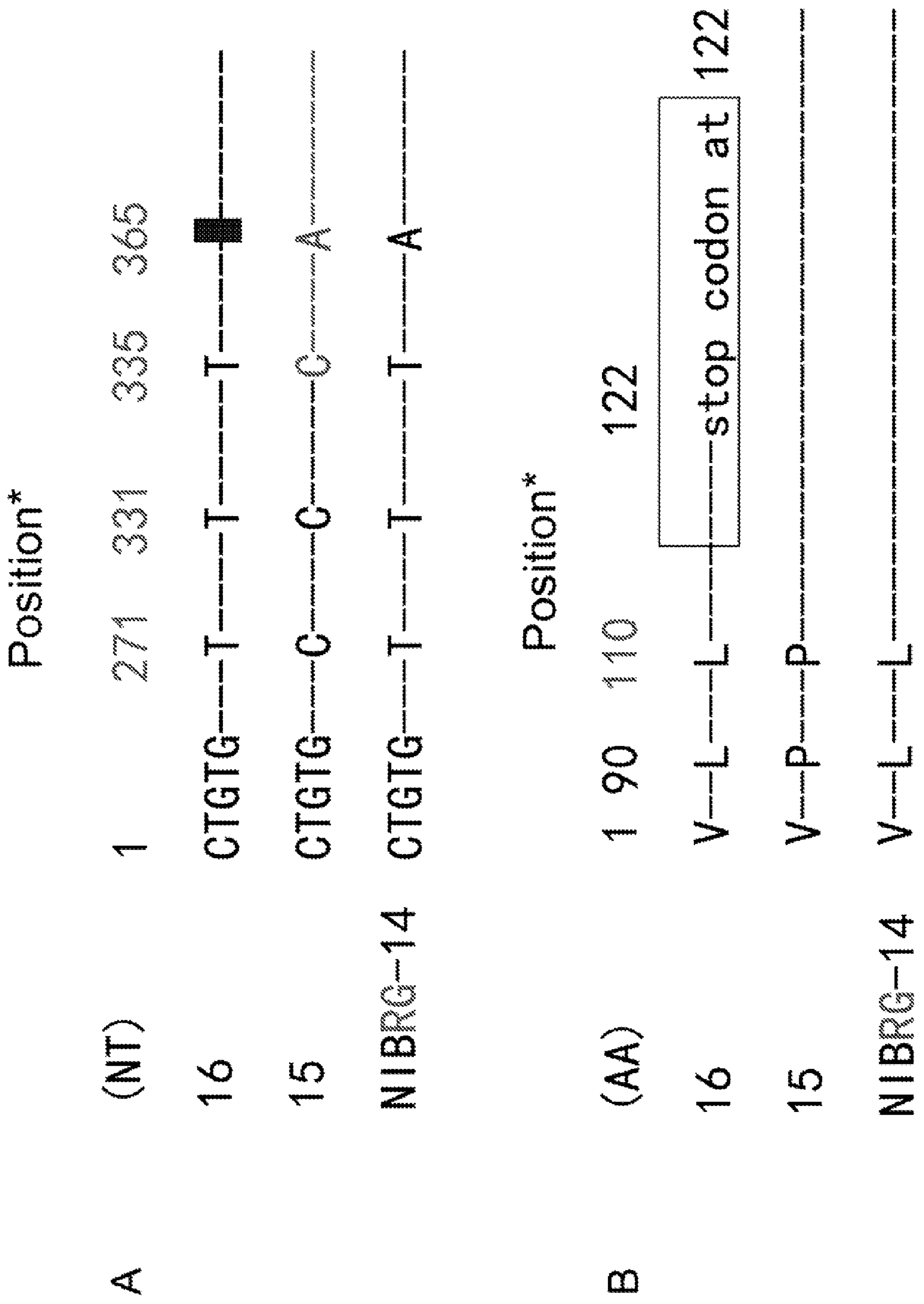
FIG. 10 illustrates the sequence alignment analysis of the amino acid (AA) sequences of the influenza virus NS protein (FIG. 10B) and their corresponding nucleotide (NT) sequences (FIG. 10A) among the strains Vero-15, Vero-16 and NIBRG-14.

As shown in FIGS. 1 and 2, the NIBRG-14 strain formed small and ambiguous plaques after 6 days post-infection in Vero cells, and the peak virus titer thereof was about $10^6$ PFU/ml. After serial passages and plaque purifications in Vero cells, the two high-growth virus clones (Vero-15 and Vero-16) were selected from big plaques. Referring to FIGS. 1, 3 and 4, these two Vero-modified virus strains Vero-15 and Vero-16 formed clear and big plaques after 3 days post-infection in Vero cells, and the peak virus titers were about $10^8$ TCID50/ml. These two Vero-modified virus strains were further used to produce virus stock in T75 or T150 flasks. The virus stocks of these two Vero-modified virus strains had similar virus titers ($1.4\times10^8$ PFU/ml and $1.86\times10^8$ TCID50/ml for the Vero-15 and $1\times10^8$ PFU/ml and $2.9\times10^8$ TCID50/ml for the Vero-16).

Determination of Virus Nucleotide Sequences and Comparison

For each of the virus strains, the virus RNA was extracted by using a commercial kit (Geneaid, Taoyuan, Taiwan). The extracted virus RNA was amplified using the one-step RT-PCR (Promega, Madison, Wis.) for HA and NA or two-step RT-PCR (Invitrogen, Rockville, Md.) for the other six gene segments. The sequences of the oligonucleotide primers used in this study were readily available based on the gene sequences of NIBRG-14. The amplified DNA was sequenced using the ABI 3730 XL DNA Analyzer (Applied Biosystems Inc., Foster City, Calif.).

A comparison of the Vero-adapted strains Vero-15 and Vero-16 with the strain NIBRG 14 was given in Table 1. Regarding the strain Vero-15, as compared with the strain NIBRG-14, there were 1 to 4 nucleotide differences in the 4 segments PB2, PB1, NS and PA, as shown in Table 1, even though the nucleotide sequences in the HA, NA, NP and M segments were not different from those of the strain NIBRG-14. Regarding the strain Vero-16, there were 1 to 5 nucleotide differences in the 6 segments PB2, PB1, PA, NS, NP and M, as shown in Table 1, even though the nucleotide sequences in HA and NA segments were not different from those of the strain NIBRG-14.

TABLE 1

| | HA | NA | PB2 | PB1 | NP | M | PA | NS |
|---|---|---|---|---|---|---|---|---|
| Vero-16-NT | 0 | 0 | 1 | 4 | 5 | 2 | 3 | −1* |
| Vero-16-AA | 0 | 0 | 1 | 1 | 3 | 1 | 1 | * |

TABLE 1-continued

| | HA | NA | PB2 | PB1 | NP | M | PA | NS |
|---|---|---|---|---|---|---|---|---|
| Vero-15-NT | 0 | 0 | 1 | 4 | 0 | 0 | 1 | 3 |
| Vero-15-AA | 0 | 0 | 1 | 1 | 0 | 0 | 1 | 2 |

*Vero-16 has a nucleotide deletion which introduces a stop codon at position 122 of SEQ ID NO: 11.
NT = Nucleotide
AA = Amino acid The sequence analyses of the amino acids (AA) and nucleotides (NT) of the segments of the three Influenza virus strains are shown in FIGS. 5 through 10.

Antigenicity Tests

To measure the antigenicity relatedness between NIBRG-14 and the Vero-modified viruses, polyclonal sheep anti-NIBRG-14 standard antisera (NIBSC) was used to measure antibody titers against NIBRG-14 and the Vero-modified virus strains using the standard hemagglutinination inhibition (HI) assay known in the art. See, for example, the WHO manual on animal influenza diagnosis and surveillance, WHO (2002)).

The antigenicity in terms of the HI titer against the strains NIBRG-14, Vero-15 and Vero-16 was determined. The results are shown in Table 2, which indicated that these three viruses had similar antigenicity. Both strains Vero-15 and Vero-16 were suitable for vaccine production.

TABLE 2

| Influenza Virus Strain | HI titer |
|---|---|
| Vero-15 | 400 |
| Vero-16 | 400 |
| NIBRG-14 (egg) | 800 |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated influenza vaccinal virus comprising:

(a) an altered PB1 protein, the altered PB1 protein having a substitution at an amino acid residue corresponding to amino acid residue Lys195 of NIBRG-14 PB1 protein (SEQ ID NO: 1), wherein the substitution in the altered PB1 protein is from Lys (K) to Leu (L);

(b) an altered PB2 protein, the altered PB2 protein having a substitution at an amino acid residue corresponding to amino acid residue Ser359 of NIBRG-14 PB2 protein (SEQ ID NO: 3), wherein the substitution in the altered PB2 protein is from Ser (S) to Tyr (Y);

(c) optionally an altered NP protein, the altered NP protein having substitutions at amino acid residues corresponding to amino acid residues Asn255, Ser410 and Ser446 of NIBRG-14 NP protein (SEQ ID NO: 5), wherein the substitutions in the altered NP protein is from Asn (N) to Asp (D) at amino acid residue 255 and Ser (S) to Phe (F) at amino acid residues 410 and 446;

(d) optionally an altered M protein, the altered M protein having a substitution at an amino acid residue corresponding to amino acid residue Leu236 of NIBRG-14 M protein (SEQ ID NO: 7), wherein the substitution in the M protein is from Leu (L) to Phe (F);

(e) an altered PA protein, the altered PA protein being selected from the group consisting of a single mutant having a substitution at an amino acid residue corresponding to amino acid residue Tyr465 and a single mutant having a substitution at an amino acid residue corresponding to amino acid residue Glu494 of NIBRG-14 PA protein (SEQ ID NO: 9), wherein the substitution at amino acid residue 465 is from Tyr (Y) to His (H), and the substitution at amino acid residue 494 is from Glu (E) to Gly (G); and (f) an altered NS protein, the altered NS protein being selected from the group consisting of a double mutant having substitutions at amino acid residues corresponding to amino acid residues Leu90 and Leu110 and a deletion mutant having a stop codon at an amino acid residue corresponding to amino acid residue Asn122 of NIBRG-14 NS protein (SEQ ID NO: 11), wherein the substitutions in the NS protein are from Leu (L) to Pro (P) at amino acid residues 90 and 110, wherein the virus exhibits increased proliferation in Vero cells compared to the H5N1 vaccine strain NIBRG-14.

2. The influenza vaccinal virus of claim 1, wherein the isolated influenza vaccinal virus comprises the altered NP protein.

3. The influenza vaccinal virus of claim 1, wherein the isolated influenza vaccinal virus comprises the altered M protein.

4. The influenza vaccinal virus of claim 1, wherein the altered PA protein comprises the amino acid residue substitute from Tyr, (Y) to His (H) at the amino acid residue 465.

5. The influenza vaccinal virus of claim 1, wherein the altered NS protein comprises the substitutions in the altered NS protein from Leu to Pro (P) at the residues 90 and 110.

6. The influenza vaccinal virus of claim 1, wherein the virus comprises:

(i) the altered NP protein;

(ii) the altered M protein;

(iii) the altered PA protein, having the substitution from Tyr (Y) to His (H); and (iv) the altered NS protein, having the stop codon at the amino acid residue corresponding to amino acid residue Asn122 of NIBRG-14 NS protein (SEQ ID NO: 11).

7. The influenza vaccinal virus of claim 1, wherein the virus has no alterations in HA and NA proteins compared to NIBRG-14 HA (SEQ ID NO: 13) and NA (SEQ ID NO: 15) proteins.

8. The influenza vaccinal virus of claim 1, wherein the virus comprises:

(i) the altered PA protein, having the substitution from Glu (E) to Gly (G); and (ii) the altered NS protein, having the substitutions from Leu (L) to Pro (P) at the amino acid residues 90 and 110;

wherein the virus has no alterations in the NP and M proteins compared to NIBRG-14 NP and M proteins.

9. The influenza vaccinal virus of claim 1, wherein the virus comprises:

(i) the altered PA protein, having the substitution from Glu (E) to Gly (G); and (ii) the altered NS protein, having the substitution from Leu (L) to Pro (P) at the amino acid residues Leu90 and Leu110.

10. The influenza vaccinal virus of claim 1, wherein the virus is type A virus.

11. The influenza vaccinal virus of claim 1, wherein the virus is H5N1 virus.

* * * * *

SEQUENCE LISTING

```
<160> NUMBER OF SEQ ID NOS: 16

<210> SEQ ID NO 1
<211> LENGTH: 753
<212> TYPE: PRT
<213> ORGANISM: Influenza A virus

<400> SEQUENCE: 1
```

-continued

```
Val Asn Pro Thr Leu Leu Phe Leu Lys Val Pro Ala Gln Asn Ala Ile
1               5                   10                  15

Ser Thr Thr Phe Pro Tyr Thr Gly Asp Pro Pro Tyr Ser His Gly Thr
            20                  25                  30

Gly Thr Gly Tyr Thr Met Asp Thr Val Asn Arg Thr His Gln Tyr Ser
        35                  40                  45

Glu Lys Gly Arg Trp Thr Thr Asn Thr Glu Thr Gly Ala Pro Gln Leu
    50                  55                  60

Asn Pro Ile Asp Gly Pro Leu Pro Glu Asp Asn Glu Pro Ser Gly Tyr
65                  70                  75                  80

Ala Gln Thr Asp Cys Val Leu Glu Ala Met Ala Phe Leu Glu Glu Ser
                85                  90                  95

His Pro Gly Ile Phe Glu Asn Ser Cys Ile Glu Thr Met Glu Val Val
            100                 105                 110

Gln Gln Thr Arg Val Asp Lys Leu Thr Gln Gly Arg Gln Thr Tyr Asp
        115                 120                 125

Trp Thr Leu Asn Arg Asn Gln Pro Ala Ala Thr Ala Leu Ala Asn Thr
    130                 135                 140

Ile Glu Val Phe Arg Ser Asn Gly Leu Thr Ala Asn Glu Ser Gly Arg
145                 150                 155                 160

Leu Ile Asp Phe Leu Lys Asp Val Met Glu Ser Met Lys Lys Glu Glu
                165                 170                 175

Met Gly Ile Thr Thr His Phe Gln Arg Lys Arg Arg Val Arg Asp Asn
            180                 185                 190

Met Thr Lys Lys Met Ile Thr Gln Arg Thr Ile Gly Lys Arg Lys Gln
        195                 200                 205

Arg Leu Asn Lys Arg Gly Tyr Leu Ile Arg Ala Leu Thr Leu Asn Thr
    210                 215                 220

Met Thr Lys Asp Ala Glu Arg Gly Lys Leu Lys Arg Arg Ala Ile Ala
225                 230                 235                 240

Thr Pro Gly Met Gln Ile Arg Gly Phe Val Tyr Phe Val Glu Thr Leu
                245                 250                 255

Ala Arg Ser Ile Cys Glu Lys Leu Glu Gln Ser Gly Leu Pro Val Gly
            260                 265                 270

Gly Asn Glu Lys Lys Ala Lys Leu Ala Asn Val Val Arg Lys Met Met
        275                 280                 285

Thr Asn Ser Gln Asp Thr Glu Leu Ser Phe Thr Ile Thr Gly Asp Asn
    290                 295                 300

Thr Lys Trp Asn Glu Asn Gln Asn Pro Arg Met Phe Leu Ala Met Ile
305                 310                 315                 320

Thr Tyr Met Thr Arg Asn Gln Pro Glu Trp Phe Arg Asn Val Leu Ser
                325                 330                 335

Ile Ala Pro Ile Met Phe Ser Asn Lys Met Ala Arg Leu Gly Lys Gly
            340                 345                 350

Tyr Met Phe Glu Ser Lys Ser Met Lys Leu Arg Thr Gln Ile Pro Ala
        355                 360                 365

Glu Met Leu Ala Ser Ile Asp Leu Lys Tyr Phe Asn Asp Ser Thr Arg
    370                 375                 380

Lys Lys Ile Glu Lys Ile Arg Pro Leu Leu Ile Glu Gly Thr Ala Ser
385                 390                 395                 400

Leu Ser Pro Gly Met Met Met Gly Met Phe Asn Met Leu Ser Thr Val
                405                 410                 415

Leu Gly Val Ser Ile Leu Asn Leu Gly Gln Lys Arg Tyr Thr Lys Thr
            420                 425                 430
```

-continued

```
Thr Tyr Trp Trp Asp Gly Leu Gln Ser Ser Asp Asp Phe Ala Leu Ile
        435                 440                 445

Val Asn Ala Pro Asn His Glu Gly Ile Gln Ala Gly Val Asp Arg Phe
    450                 455                 460

Tyr Arg Thr Cys Lys Leu Leu Gly Ile Asn Met Ser Lys Lys Lys Ser
465                 470                 475                 480

Tyr Ile Asn Arg Thr Gly Thr Phe Glu Phe Thr Ser Phe Phe Tyr Arg
                485                 490                 495

Tyr Gly Phe Val Ala Asn Phe Ser Met Glu Leu Pro Ser Phe Gly Val
            500                 505                 510

Ser Gly Ile Asn Glu Ser Ala Asp Met Ser Ile Gly Val Thr Val Ile
        515                 520                 525

Lys Asn Asn Met Ile Asn Asn Asp Leu Gly Pro Ala Thr Ala Gln Met
    530                 535                 540

Ala Leu Gln Leu Phe Ile Lys Asp Tyr Arg Tyr Thr Tyr Arg Cys His
545                 550                 555                 560

Arg Gly Asp Thr Gln Ile Gln Thr Arg Arg Ser Phe Glu Ile Lys Lys
                565                 570                 575

Leu Trp Glu Gln Thr Arg Ser Lys Ala Gly Leu Leu Val Ser Asp Gly
            580                 585                 590

Gly Pro Asn Leu Tyr Asn Ile Arg Asn Leu His Ile Pro Glu Val Cys
        595                 600                 605

Leu Lys Trp Glu Leu Met Asp Glu Asp Tyr Gln Gly Arg Leu Cys Asn
    610                 615                 620

Pro Leu Asn Pro Phe Val Ser His Lys Glu Ile Glu Ser Met Asn Asn
625                 630                 635                 640

Ala Val Met Met Pro Ala His Gly Pro Ala Lys Asn Met Glu Tyr Asp
                645                 650                 655

Ala Val Ala Thr Thr His Ser Trp Ile Pro Lys Arg Asn Arg Ser Ile
            660                 665                 670

Leu Asn Thr Ser Gln Arg Gly Val Leu Glu Asp Glu Gln Met Tyr Gln
        675                 680                 685

Arg Cys Cys Asn Leu Phe Glu Lys Phe Phe Pro Ser Ser Ser Tyr Arg
    690                 695                 700

Arg Pro Val Gly Ile Ser Ser Met Val Glu Ala Met Val Ser Arg Ala
705                 710                 715                 720

Arg Ile Asp Ala Arg Ile Asp Phe Glu Ser Gly Arg Ile Lys Lys Glu
                725                 730                 735

Glu Phe Thr Glu Ile Met Lys Ile Cys Ser Thr Ile Glu Glu Leu Arg
            740                 745                 750

Arg
```

```
<210> SEQ ID NO 2
<211> LENGTH: 2258
<212> TYPE: DNA
<213> ORGANISM: Influenza A virus

<400> SEQUENCE: 2

gtcaatccga ccttactttt cttaaaagtg ccagcacaaa atgctataag cacaactttc      60

ccttataccg gagaccctcc ttacagccat gggacaggaa caggatacac catggatact     120

gtcaacagga cacatcagta ctcagaaaag ggaagatgga caacaaacac cgaaactgga     180

gcaccgcaac tcaacccgat tgatgggcca ctgccagaag acaatgaacc aagtggttat     240

gcccaaacag attgtgtatt ggaagcaatg gctttccttg aggaatccca tcctggtatt     300
```

-continued

```
tttgaaaact cgtgtattga aacgatggag gttgttcagc aaacacgagt agacaagctg    360
acacaaggcc gacagaccta tgactggact ttaaatagaa accagcctgc tgcaacagca    420
ttggccaaca caatagaagt gttcagatca aatggcctca cggccaatga gtcaggaagg    480
ctcatagact tccttaagga tgtaatggag tcaatgaaaa aagaagaaat ggggatcaca    540
actcattttc agagaaagag acgggtgaga gacaatatga ctaagaaaat gataacacag    600
agaacaatag gtaaaaggaa acagagattg aacaaaaggg gttatctaat tagagcattg    660
accctgaaca caatgaccaa agatgctgag agagggaagc taaaacggag agcaattgca    720
accccaggga tgcaaataag gggggtttgta tactttgttg agacactggc aaggagtata    780
tgtgagaaac ttgaacaatc agggttgcca gttggaggca atgagaagaa agcaaagttg    840
gcaaatgttg taaggaagat gatgaccaat tctcaggaca ccgaactttc tttcaccatc    900
actggagata acaccaaatg gaacgaaaat cagaatcctc ggatgttttt ggccatgatc    960
acatatatga ccagaaatca gcccgaatgg ttcagaaatg ttctaagtat tgctccaata   1020
atgttctcaa acaaaatggc gagactggga aaagggtata tgtttgagag caagagtatg   1080
aaacttagaa ctcaaatacc tgcagaaatg ctagcaagca ttgatttgaa atatttcaat   1140
gattcaacaa gaaagaagat tgaaaaaatc cgaccgctct taatagaggg gactgcatca   1200
ttgagccctg gaatgatgat gggcatgttc aatatgttaa gcactgtatt aggcgtctcc   1260
atcctgaatc ttggacaaaa gagatacacc aagactactt actggtggga tggtcttcaa   1320
tcctctgacg attttgctct gattgtgaat gcacccaatc atgaagggat tcaagccgga   1380
gtcgacaggt tttatcgaac ctgtaagcta cttggaatca atatgagcaa gaaaaagtct   1440
tacataaaca gaacaggtac atttgaattc acaagttttt tctatcgtta tgggtttgtt   1500
gccaatttca gcatggagct tcccagtttt ggggtgtctg ggatcaacga gtcagcggac   1560
atgagtattg gagttactgt catcaaaaac aatatgataa acaatgatct tggtccagca   1620
acagctcaaa tggcccttca gttgttcatc aaagattaca ggtacacgta ccgatgccat   1680
agaggtgaca cacaaataca aacccgaaga tcatttgaaa taaagaaact gtgggagcaa   1740
acccgttcca aagctggact gctggtctcc gacggaggcc caaatttata caacattaga   1800
aatctccaca ttcctgaagt ctgcctaaaa tgggaattga tggatgagga ttaccagggg   1860
cgtttatgca acccactgaa cccatttgtc agccataaag aaattgaatc aatgaacaat   1920
gcagtgatga tgccagcaca tggtccagcc aaaaacatgg agtatgatgc tgttgcaaca   1980
acacactcct ggatccccaa aagaaatcga tccatcttga atacaagtca aagaggagta   2040
cttgaagatg aacaaatgta ccaaaggtgc tgcaatttat ttgaaaaatt cttccccagc   2100
agttcataca gaagaccagt cgggatatcc agtatggtgg aggctatggt ttccagagcc   2160
cgaattgatg cacggattga tttcgaatct ggaaggataa agaaagaaga gttcactgag   2220
atcatgaaga tctgttccac cattgaagag ctcagacg                           2258
```

<210> SEQ ID NO 3
<211> LENGTH: 762
<212> TYPE: PRT
<213> ORGANISM: Influenza A virus

<400> SEQUENCE: 3

```
Glu Arg Ile Lys Glu Leu Arg Asn Leu Met Ser Gln Ser Arg Thr Arg
1               5                   10                  15

Glu Ile Leu Thr Lys Thr Thr Val Asp His Met Ala Ile Ile Lys Lys
            20                  25                  30
```

-continued

```
Tyr Thr Ser Gly Arg Gln Glu Lys Asn Pro Ala Leu Arg Met Lys Trp
        35                  40                  45

Met Met Ala Met Lys Tyr Pro Ile Thr Ala Asp Lys Arg Ile Thr Glu
    50                  55                  60

Met Ile Pro Glu Arg Asn Glu Gln Gly Gln Thr Leu Trp Ser Lys Met
65                  70                  75                  80

Asn Asp Ala Gly Ser Asp Arg Val Met Val Ser Pro Leu Ala Val Thr
                85                  90                  95

Trp Trp Asn Arg Asn Gly Pro Met Thr Asn Thr Val His Tyr Pro Lys
            100                 105                 110

Ile Tyr Lys Thr Tyr Phe Glu Arg Val Glu Arg Leu Lys His Gly Thr
        115                 120                 125

Phe Gly Pro Val His Phe Arg Asn Gln Val Lys Ile Arg Arg Arg Val
    130                 135                 140

Asp Ile Asn Pro Gly His Ala Asp Leu Ser Ala Lys Glu Ala Gln Asp
145                 150                 155                 160

Val Ile Met Glu Val Val Phe Pro Asn Glu Val Gly Ala Arg Ile Leu
                165                 170                 175

Thr Ser Glu Ser Gln Leu Thr Ile Thr Lys Glu Lys Lys Glu Glu Leu
            180                 185                 190

Gln Asp Cys Lys Ile Ser Pro Leu Met Val Ala Tyr Met Leu Glu Arg
        195                 200                 205

Glu Leu Val Arg Lys Thr Arg Phe Leu Pro Val Ala Gly Gly Thr Ser
    210                 215                 220

Ser Val Tyr Ile Glu Val Leu His Leu Thr Gln Gly Thr Cys Trp Glu
225                 230                 235                 240

Gln Met Tyr Thr Pro Gly Gly Glu Val Lys Asn Asp Asp Val Asp Gln
                245                 250                 255

Ser Leu Ile Ile Ala Ala Arg Asn Ile Val Arg Arg Ala Ala Val Ser
            260                 265                 270

Ala Asp Pro Leu Ala Ser Leu Leu Glu Met Cys His Ser Thr Gln Ile
        275                 280                 285

Gly Gly Ile Arg Met Val Asp Ile Leu Lys Gln Asn Pro Thr Glu Glu
    290                 295                 300

Gln Ala Val Asp Ile Cys Lys Ala Ala Met Gly Leu Arg Ile Ser Ser
305                 310                 315                 320

Ser Phe Ser Phe Gly Gly Phe Thr Phe Lys Arg Thr Ser Gly Ser Ser
                325                 330                 335

Val Lys Arg Glu Glu Glu Val Leu Thr Gly Asn Leu Gln Thr Leu Lys
            340                 345                 350

Ile Arg Val His Glu Gly Ser Glu Glu Phe Thr Met Val Gly Arg Arg
        355                 360                 365

Ala Thr Ala Ile Leu Arg Lys Ala Thr Arg Arg Leu Ile Gln Leu Ile
    370                 375                 380

Val Ser Gly Arg Asp Glu Gln Ser Ile Ala Glu Ala Ile Ile Val Ala
385                 390                 395                 400

Met Val Phe Ser Gln Glu Asp Cys Met Ile Lys Ala Val Arg Gly Asp
                405                 410                 415

Leu Asn Phe Val Asn Arg Ala Asn Gln Arg Leu Asn Pro Met His Gln
            420                 425                 430

Leu Leu Arg His Phe Gln Lys Asp Ala Lys Val Leu Phe Gln Asn Trp
        435                 440                 445

Gly Val Glu Pro Ile Asp Asn Val Met Gly Met Ile Gly Ile Leu Pro
```

```
    450                 455                 460

Asp Met Thr Pro Ser Ile Glu Met Ser Met Arg Gly Val Arg Ile Ser
465                 470                 475                 480

Lys Met Gly Val Asp Glu Tyr Ser Ser Thr Glu Arg Val Val Val Ser
                485                 490                 495

Ile Asp Arg Phe Leu Arg Val Arg Asp Gln Arg Gly Asn Val Leu Leu
            500                 505                 510

Ser Pro Glu Glu Val Ser Glu Thr Gln Gly Thr Glu Lys Leu Thr Ile
        515                 520                 525

Thr Tyr Ser Ser Ser Met Met Trp Glu Ile Asn Gly Pro Glu Ser Val
    530                 535                 540

Leu Val Asn Thr Tyr Gln Trp Ile Ile Arg Asn Trp Glu Thr Val Lys
545                 550                 555                 560

Ile Gln Trp Ser Gln Asn Pro Thr Met Leu Tyr Asn Lys Met Glu Phe
                565                 570                 575

Glu Pro Phe Gln Ser Leu Val Pro Lys Ala Ile Arg Gly Gln Tyr Ser
            580                 585                 590

Gly Phe Val Arg Thr Leu Phe Gln Gln Met Arg Asp Val Leu Gly Thr
        595                 600                 605

Phe Asp Thr Ala Gln Ile Ile Lys Leu Leu Pro Phe Ala Ala Ala Pro
    610                 615                 620

Pro Lys Gln Ser Arg Met Gln Phe Ser Ser Phe Thr Val Asn Val Arg
625                 630                 635                 640

Gly Ser Gly Met Arg Ile Leu Val Arg Gly Asn Ser Pro Val Phe Asn
                645                 650                 655

Tyr Asn Lys Ala Thr Lys Arg Leu Thr Val Leu Gly Lys Asp Ala Gly
            660                 665                 670

Thr Leu Thr Glu Asp Pro Asp Glu Gly Thr Ala Gly Val Glu Ser Ala
        675                 680                 685

Val Leu Arg Gly Phe Leu Ile Leu Gly Lys Glu Asp Arg Arg Tyr Gly
    690                 695                 700

Pro Ala Leu Ser Ile Asn Glu Leu Ser Asn Leu Ala Lys Gly Glu Lys
705                 710                 715                 720

Ala Asn Val Leu Ile Gly Gln Gly Asp Val Val Leu Val Met Lys Arg
                725                 730                 735

Lys Arg Asp Ser Ser Ile Leu Thr Asp Ser Gln Thr Ala Thr Lys Arg
            740                 745                 750

Ile Arg Met Ala Ile Asn Cys Arg Ile Val
        755                 760


<210> SEQ ID NO 4
<211> LENGTH: 2286
<212> TYPE: DNA
<213> ORGANISM: Influenza A virus

<400> SEQUENCE: 4

gaaagaataa aagaactaag aaatctaatg tcgcagtctc gcacccgcga gatactcaca      60

aaaaccaccg tggaccatat ggccataatc aagaagtaca catcaggaag acaggagaag     120

aacccagcac ttaggatgaa atggatgatg gcaatgaaat atccaattac agcagacaag     180

aggataacgg aaatgattcc tgagagaaat gagcaaggac aaactttatg gagtaaaatg     240

aatgatgccg gatcagaccg agtgatggta tcacctctgg ctgtgacatg gtggaatagg     300

aatggaccaa tgacaaatac agttcattat ccaaaaatct acaaaactta ttttgaaaga     360

gtcgaaaggc taaagcatgg aacctttggc cctgtccatt ttagaaacca agtcaaaata     420
```

-continued

```
cgtcggagag ttgacataaa tcctggtcat gcagatctca gtgccaagga ggcacaggat    480

gtaatcatgg aagttgtttt ccctaacgaa gtgggagcca ggatactaac atcggaatcg    540

caactaacga taaccaaaga gaagaaagaa gaactccagg attgcaaaat ttctcctttg    600

atggttgcat acatgttgga gagagaactg gtccgcaaaa cgagattcct cccagtggct    660

ggtggaacaa gcagtgtgta cattgaagtg ttgcatttga ctcaaggaac atgctgggaa    720

cagatgtata ctccaggagg ggaagtgaag aatgatgatg ttgatcaaag cttgattatt    780

gctgctagga acatagtgag aagagctgca gtatcagcag acccactagc atctttattg    840

gagatgtgcc acagcacaca gattggtgga attaggatgg tagacatcct taagcagaac    900

ccaacagaag agcaagccgt ggatatatgc aaggctgcaa tgggactgag aattagctca    960

tccttcagtt ttggtggatt cacatttaag agaacaagcg gatcatcagt caagagagag   1020

gaagaggtgc ttacgggcaa tcttcaaaca ttgaagataa gagtgcatga gggatctgaa   1080

gagttcacaa tggttgggag aagagcaaca gccatactca gaaaagcaac caggagattg   1140

attcagctga tagtgagtgg gagagacgaa cagtcgattg ccgaagcaat aattgtggcc   1200

atggtatttt cacaagagga ttgtatgata aaagcagtta gaggtgatct gaatttcgtc   1260

aatagggcga atcagcgact gaatcctatg catcaacttt taagacattt tcagaaggat   1320

gcgaaagtgc tttttcaaaa ttggggagtt gaacctatcg acaatgtgat gggaatgatt   1380

gggatattgc ccgacatgac tccaagcatc gagatgtcaa tgagaggagt gagaatcagc   1440

aaaatgggtg tagatgagta ctccagcacg gagagggtag tggtgagcat tgaccggttc   1500

ttgagagtca gggaccaacg aggaaatgta ctactgtctc ccgaggaggt cagtgaaaca   1560

cagggaacag agaaactgac aataacttac tcatcgtcaa tgatgtggga gattaatggt   1620

cctgaatcag tgttggtcaa tacctatcaa tggatcatca gaaactggga aactgttaaa   1680

attcagtggt cccagaaccc tacaatgcta tacaataaaa tggaatttga accatttcag   1740

tctttagtac ctaaggccat tagaggccaa tacagtgggt ttgtaagaac tctgttccaa   1800

caaatgaggg atgtgcttgg gacatttgat accgcacaga taataaaact tcttcccttc   1860

gcagccgctc caccaaagca aagtagaatg cagttctcct catttactgt gaatgtgagg   1920

ggatcaggaa tgagaatact tgtaaggggc aattctcctg tattcaacta caacaaggcc   1980

acgaagagac tcacagttct cggaaaggat gctggcactt taaccgaaga cccagatgaa   2040

ggcacagctg gagtggagtc cgctgttctg aggggattcc tcattctggg caaagaagac   2100

aggagatatg ggccagcatt aagcatcaat gaactgagca accttgcgaa aggagagaag   2160

gctaatgtgc taattgggca aggagacgtg gtgttggtaa tgaaacgaaa acgggactct   2220

agcatactta ctgacagcca gacagcgacc aaaagaattc ggatggccat caattagtgt   2280

cgaata                                                              2286
```

<210> SEQ ID NO 5
<211> LENGTH: 505
<212> TYPE: PRT
<213> ORGANISM: Influenza A virus
<220> FEATURE:
<221> NAME/KEY: misc_feature
<222> LOCATION: (505)..(505)
<223> OTHER INFORMATION: Xaa can be any naturally occurring amino acid

<400> SEQUENCE: 5

```
His Ser Leu Ser Asp Ile Lys Ile Met Ala Ser Gln Gly Thr Lys Arg
1               5                   10                  15
```

-continued

```
Ser Tyr Glu Gln Met Glu Thr Asp Gly Glu Arg Gln Asn Ala Thr Glu
            20                  25                  30

Ile Arg Ala Ser Val Gly Lys Met Ile Gly Gly Ile Gly Arg Phe Tyr
        35                  40                  45

Ile Gln Met Cys Thr Glu Leu Lys Leu Ser Asp Tyr Glu Gly Arg Leu
    50                  55                  60

Ile Gln Asn Ser Leu Thr Ile Glu Arg Met Val Leu Ser Ala Phe Asp
65                  70                  75                  80

Glu Arg Arg Asn Lys Tyr Leu Glu Glu His Pro Ser Ala Gly Lys Asp
                85                  90                  95

Pro Lys Lys Thr Gly Gly Pro Ile Tyr Arg Arg Val Asn Gly Lys Trp
            100                 105                 110

Met Arg Glu Leu Ile Leu Tyr Asp Lys Glu Glu Ile Arg Arg Ile Trp
        115                 120                 125

Arg Gln Ala Asn Asn Gly Asp Asp Ala Thr Ala Gly Leu Thr His Met
    130                 135                 140

Met Ile Trp His Ser Asn Leu Asn Asp Ala Thr Tyr Gln Arg Thr Arg
145                 150                 155                 160

Ala Leu Val Arg Thr Gly Met Asp Pro Arg Met Cys Ser Leu Met Gln
                165                 170                 175

Gly Ser Thr Leu Pro Arg Arg Ser Gly Ala Ala Gly Ala Ala Val Lys
            180                 185                 190

Gly Val Gly Thr Met Val Met Glu Leu Val Arg Met Ile Lys Arg Gly
        195                 200                 205

Ile Asn Asp Arg Asn Phe Trp Arg Gly Glu Asn Gly Arg Lys Thr Arg
    210                 215                 220

Ile Ala Tyr Glu Arg Met Cys Asn Ile Leu Lys Gly Lys Phe Gln Thr
225                 230                 235                 240

Ala Ala Gln Lys Ala Met Met Asp Gln Val Arg Glu Ser Arg Asn Pro
                245                 250                 255

Gly Asn Ala Glu Phe Glu Asp Leu Thr Phe Leu Ala Arg Ser Ala Leu
            260                 265                 270

Ile Leu Arg Gly Ser Val Ala His Lys Ser Cys Leu Pro Ala Cys Val
        275                 280                 285

Tyr Gly Pro Ala Val Ala Ser Gly Tyr Asp Phe Glu Arg Glu Gly Tyr
    290                 295                 300

Ser Leu Val Gly Ile Asp Pro Phe Arg Leu Leu Gln Asn Ser Gln Val
305                 310                 315                 320

Tyr Ser Leu Ile Arg Pro Asn Glu Asn Pro Ala His Lys Ser Gln Leu
                325                 330                 335

Val Trp Met Ala Cys His Ser Ala Ala Phe Glu Asp Leu Arg Val Leu
            340                 345                 350

Ser Phe Ile Lys Gly Thr Lys Val Val Pro Arg Gly Lys Leu Ser Thr
        355                 360                 365

Arg Gly Val Gln Ile Ala Ser Asn Glu Asn Met Glu Thr Met Glu Ser
    370                 375                 380

Ser Thr Leu Glu Leu Arg Ser Arg Tyr Trp Ala Ile Arg Thr Arg Ser
385                 390                 395                 400

Gly Gly Asn Thr Asn Gln Gln Arg Ala Ser Ala Gly Gln Ile Ser Ile
                405                 410                 415

Gln Pro Thr Phe Ser Val Gln Arg Asn Leu Pro Phe Asp Arg Thr Thr
            420                 425                 430

Val Met Ala Ala Phe Thr Gly Asn Thr Glu Gly Arg Thr Ser Asp Met
        435                 440                 445
```

-continued

Arg Thr Glu Ile Ile Arg Met Met Glu Ser Ala Arg Pro Glu Asp Val
450 455 460

Ser Phe Gln Gly Arg Gly Val Phe Glu Leu Ser Asp Glu Lys Ala Ala
465 470 475 480

Ser Pro Ile Val Pro Ser Phe Asp Met Ser Asn Glu Gly Ser Tyr Phe
485 490 495

Phe Gly Asp Asn Ala Glu Glu Tyr Xaa
500 505

<210> SEQ ID NO 6
<211> LENGTH: 1513
<212> TYPE: DNA
<213> ORGANISM: Influenza A virus

<400> SEQUENCE: 6
cactcactga gtgacatcaa aatcatggcg tcccaaggca ccaaacggtc ttacgaacag 60
atggagactg atggagaacg ccagaatgcc actgaaatca gagcatccgt cggaaaaatg 120
attggtggaa ttggacgatt ctacatccaa atgtgcacag aacttaaact cagtgattat 180
gagggacggt tgatccaaaa cagcttaaca atagagagaa tggtgctctc tgcttttgac 240
gaaaggagaa ataaatacct ggaagaacat cccagtgcgg ggaaagatcc taagaaaact 300
ggaggaccta tatacagaag agtaaacgga aagtggatga gagaactcat cctttatgac 360
aaagaagaaa taaggcgaat ctggcgccaa gctaataatg gtgacgatgc aacggctggt 420
ctgactcaca tgatgatctg gcattccaat ttgaatgatg caacttatca gaggacaagg 480
gctcttgttc gcaccggaat ggatcccagg atgtgctctc tgatgcaagg ttcaactctc 540
cctaggaggt ctggagccgc aggtgctgca gtcaaaggag ttggaacaat ggtgatggaa 600
ttggtcagga tgatcaaacg tgggatcaat gatcggaact tctggagggg tgagaatgga 660
cgaaaaacaa gaattgctta tgaaagaatg tgcaacattc tcaaagggaa atttcaaact 720
gctgcacaaa aagcaatgat ggatcaagtg agagagagcc ggaacccagg gaatgctgag 780
ttcgaagatc tcacttttct agcacggtct gcactcatat tgagagggtc ggttgctcac 840
aagtcctgcc tgcctgcctg tgtgtatgga cctgccgtag ccagtgggta cgactttgaa 900
agagagggat actctctagt cggaatagac cctttcagac tgcttcaaaa cagccaagtg 960
tacagcctaa tcagaccaaa tgagaatcca gcacacaaga gtcaactggt gtggatggca 1020
tgccattctg ccgcatttga agatctaaga gtattgagct tcatcaaagg gacgaaggtg 1080
gtcccaagag ggaagctttc cactagagga gttcaaattg cttccaatga aaatatggag 1140
actatggaat caagtacact tgaactgaga agcaggtact gggccataag gaccagaagt 1200
ggaggaaaca ccaatcaaca gagggcatct gcgggccaaa tcagcataca acctacgttc 1260
tcagtacaga gaaatctccc ttttgacaga acaaccgtta tggcagcatt cactgggaat 1320
acagagggga gaacatctga catgaggacc gaaatcataa ggatgatgga aagtgcaaga 1380
ccagaagatg tgtctttcca ggggcgggga gtcttcgagc tctcggacga aaaggcagcg 1440
agcccgatcg tgccttcctt tgacatgagt aatgaaggat cttatttctt cggagacaat 1500
gcagaggagt acg 1513

<210> SEQ ID NO 7
<211> LENGTH: 327
<212> TYPE: PRT
<213> ORGANISM: Influenza A virus
<220> FEATURE:
<221> NAME/KEY: misc_feature

```
<222> LOCATION: (327)..(327)
<223> OTHER INFORMATION: Xaa can be any naturally occurring amino acid

<400> SEQUENCE: 7

Tyr Lys Met Ser Leu Leu Thr Glu Val Glu Thr Tyr Val Leu Ser Ile
1               5                   10                  15

Ile Pro Ser Gly Pro Leu Lys Ala Glu Ile Ala Gln Arg Leu Glu Asp
            20                  25                  30

Val Phe Ala Gly Lys Asn Thr Asp Leu Glu Val Leu Met Glu Trp Leu
        35                  40                  45

Lys Thr Arg Pro Ile Leu Ser Pro Leu Thr Lys Gly Ile Leu Gly Phe
    50                  55                  60

Val Phe Thr Leu Thr Val Pro Ser Glu Arg Gly Leu Gln Arg Arg Arg
65                  70                  75                  80

Phe Val Gln Asn Ala Leu Asn Gly Asn Gly Asp Pro Asn Asn Met Asp
                85                  90                  95

Lys Ala Val Lys Leu Tyr Arg Lys Leu Lys Arg Glu Ile Thr Phe His
            100                 105                 110

Gly Ala Lys Glu Ile Ser Leu Ser Tyr Ser Ala Gly Ala Leu Ala Ser
        115                 120                 125

Cys Met Gly Leu Ile Tyr Asn Arg Met Gly Ala Val Thr Thr Glu Val
    130                 135                 140

Ala Phe Gly Leu Val Cys Ala Thr Cys Glu Gln Ile Ala Asp Ser Gln
145                 150                 155                 160

His Arg Ser His Arg Gln Met Val Thr Thr Thr Asn Pro Leu Ile Arg
                165                 170                 175

His Glu Asn Arg Met Val Leu Ala Ser Thr Thr Ala Lys Ala Met Glu
            180                 185                 190

Gln Met Ala Gly Ser Ser Glu Gln Ala Ala Glu Ala Met Glu Val Ala
        195                 200                 205

Ser Gln Ala Arg Gln Met Val Gln Ala Met Arg Thr Ile Gly Thr His
    210                 215                 220

Pro Ser Ser Ser Ala Gly Leu Lys Asn Asp Leu Leu Glu Asn Leu Gln
225                 230                 235                 240

Ala Tyr Gln Lys Arg Met Gly Val Gln Met Gln Arg Phe Lys Ser Ser
                245                 250                 255

Arg Tyr Cys Arg Lys Tyr His Trp Asp Leu Ala Leu Asp Ile Val Asp
            260                 265                 270

Ser Ser Ser Phe Phe Gln Met His Leu Pro Ser Leu Ile Arg Thr Glu
        275                 280                 285

Arg Arg Ala Phe Tyr Gly Arg Ser Ala Lys Val Tyr Glu Gly Arg Ile
    290                 295                 300

Ser Lys Gly Thr Ala Glu Cys Cys Gly Cys Arg Trp Ser Phe Cys Gln
305                 310                 315                 320

His Arg Ala Gly Val Lys Xaa
                325


<210> SEQ ID NO 8
<211> LENGTH: 995
<212> TYPE: DNA
<213> ORGANISM: Influenza A virus

<400> SEQUENCE: 8

tattgaaaga tgagtcttct aaccgaggtc gaaacgtacg ttctctctat catcccgtca      60

ggccccctca aagccgagat cgcacagaga cttgaagatg tctttgcagg gaagaacacc     120
```

-continued

```
gatcttgagg ttctcatgga atggctaaag acaagaccaa tcctgtcacc tctgactaag    180

gggattttag gatttgtgtt cacgctcacc gtgcccagtg agcgaggact gcagcgtaga    240

cgctttgtcc aaaatgccct taatgggaac ggggatccaa ataacatgga caaagcagtt    300

aaactgtata ggaagctcaa gagggagata acattccatg gggccaaaga aatctcactc    360

agttattctg ctggtgcact tgccagttgt atgggcctca tatacaacag gatgggggct    420

gtgaccactg aagtggcatt tggcctggta tgtgcaacct gtgaacagat tgctgactcc    480

cagcatcggt ctcataggca aatggtgaca acaaccaacc cactaatcag acatgagaac    540

agaatggttt tagccagcac tacagctaag gctatggagc aaatggctgg atcgagtgag    600

caagcagcag aggccatgga ggttgctagt caggctaggc aaatggtgca agcgatgaga    660

accattggga ctcatcctag ctccagtgct ggtctgaaaa atgatcttct tgaaaatttg    720

caggcctatc agaaacgaat gggggtgcag atgcaacggt tcaagtgatc ctctcgctat    780

tgccgcaaat atcattggga tcttgcactt gatattgtgg attcttgatc gtcttttttt    840

caaatgcatt taccgtcgct ttaaatacgg actgaaagga gggccttcta cggaaggagt    900

gccaaagtct atgagggaag aatatcgaaa ggaacagcag agtgctgtgg atgctgacga    960

tggtcatttt gtcagcatag agctggagta aaaaa                                995
```

<210> SEQ ID NO 9
<211> LENGTH: 724
<212> TYPE: PRT
<213> ORGANISM: Influenza A virus

<400> SEQUENCE: 9

```
Lys Met Glu Asp Phe Val Arg Gln Cys Phe Asn Pro Met Ile Val Glu
1               5                   10                  15

Leu Ala Glu Lys Thr Met Lys Glu Tyr Gly Glu Asp Leu Lys Ile Glu
            20                  25                  30

Thr Asn Lys Phe Ala Ala Ile Cys Thr His Leu Glu Val Cys Phe Met
        35                  40                  45

Tyr Ser Asp Phe His Phe Ile Asn Glu Gln Gly Glu Ser Ile Ile Val
    50                  55                  60

Glu Leu Gly Asp Pro Asn Ala Leu Leu Lys His Arg Phe Glu Ile Ile
65                  70                  75                  80

Glu Gly Arg Asp Arg Thr Met Ala Trp Thr Val Val Asn Ser Ile Cys
                85                  90                  95

Asn Thr Thr Gly Ala Glu Lys Pro Lys Phe Leu Pro Asp Leu Tyr Asp
            100                 105                 110

Tyr Lys Glu Asn Arg Phe Ile Glu Ile Gly Val Thr Arg Arg Glu Val
        115                 120                 125

His Ile Tyr Tyr Leu Glu Lys Ala Asn Lys Ile Lys Ser Glu Lys Thr
    130                 135                 140

His Ile His Ile Phe Ser Phe Thr Gly Glu Glu Met Ala Thr Arg Ala
145                 150                 155                 160

Asp Tyr Thr Leu Asp Glu Glu Ser Arg Ala Arg Ile Lys Thr Arg Leu
                165                 170                 175

Phe Thr Ile Arg Gln Glu Met Ala Ser Arg Gly Leu Trp Asp Ser Phe
            180                 185                 190

Arg Gln Ser Glu Arg Gly Glu Glu Thr Ile Glu Glu Arg Phe Glu Ile
        195                 200                 205

Thr Gly Thr Met Arg Lys Leu Ala Asp Gln Ser Leu Pro Pro Asn Phe
    210                 215                 220
```

Ser Ser Leu Glu Asn Phe Arg Ala Tyr Val Asp Gly Phe Glu Pro Asn
225 230 235 240

Gly Tyr Ile Glu Gly Lys Leu Ser Gln Met Ser Lys Glu Val Asn Ala
245 250 255

Arg Ile Glu Pro Phe Leu Lys Thr Thr Pro Arg Pro Leu Arg Leu Pro
260 265 270

Asn Gly Pro Pro Cys Ser Gln Arg Ser Lys Phe Leu Leu Met Asp Ala
275 280 285

Leu Lys Leu Ser Ile Glu Asp Pro Ser His Glu Gly Glu Gly Ile Pro
290 295 300

Leu Tyr Asp Ala Ile Lys Cys Met Arg Thr Phe Phe Gly Trp Lys Glu
305 310 315 320

Pro Asn Val Val Lys Pro His Glu Lys Gly Ile Asn Pro Asn Tyr Leu
325 330 335

Leu Ser Trp Lys Gln Val Leu Ala Glu Leu Gln Asp Ile Glu Asn Glu
340 345 350

Glu Lys Ile Pro Lys Thr Lys Asn Met Lys Lys Thr Ser Gln Leu Lys
355 360 365

Trp Ala Leu Gly Glu Asn Met Ala Pro Glu Lys Val Asp Phe Asp Asp
370 375 380

Cys Lys Asp Val Gly Asp Leu Lys Gln Tyr Asp Ser Asp Glu Pro Glu
385 390 395 400

Leu Arg Ser Leu Ala Ser Trp Ile Gln Asn Glu Phe Asn Lys Ala Cys
405 410 415

Glu Leu Thr Asp Ser Ser Trp Ile Glu Leu Asp Glu Ile Gly Glu Asp
420 425 430

Val Ala Pro Ile Glu His Ile Ala Ser Met Arg Arg Asn Tyr Phe Thr
435 440 445

Ser Glu Val Ser His Cys Arg Ala Thr Glu Tyr Ile Met Lys Gly Val
450 455 460

Tyr Ile Asn Thr Ala Leu Leu Asn Ala Ser Cys Ala Ala Met Asp Asp
465 470 475 480

Phe Gln Leu Ile Pro Met Ile Ser Lys Cys Arg Thr Lys Glu Gly Arg
485 490 495

Arg Lys Thr Asn Leu Tyr Gly Phe Ile Ile Lys Gly Arg Ser His Leu
500 505 510

Arg Asn Asp Thr Asp Val Val Asn Phe Val Ser Met Glu Phe Ser Leu
515 520 525

Thr Asp Pro Arg Leu Glu Pro His Lys Trp Glu Lys Tyr Cys Val Leu
530 535 540

Glu Ile Gly Asp Met Leu Leu Arg Ser Ala Ile Gly Gln Val Ser Arg
545 550 555 560

Pro Met Phe Leu Tyr Val Arg Thr Asn Gly Thr Ser Lys Ile Lys Met
565 570 575

Lys Trp Gly Met Glu Met Arg Arg Cys Leu Leu Gln Ser Leu Gln Gln
580 585 590

Ile Glu Ser Met Ile Glu Ala Glu Ser Ser Val Lys Glu Lys Asp Met
595 600 605

Thr Lys Glu Phe Phe Glu Asn Lys Ser Glu Thr Trp Pro Ile Gly Glu
610 615 620

Ser Pro Lys Gly Val Glu Glu Ser Ser Ile Gly Lys Val Cys Arg Thr
625 630 635 640

Leu Leu Ala Lys Ser Val Phe Asn Ser Leu Tyr Ala Ser Pro Gln Leu
645 650 655

Glu Gly Phe Ser Ala Glu Ser Arg Lys Leu Leu Leu Ile Val Gln Ala
660 665 670

Leu Arg Asp Asn Leu Glu Pro Gly Thr Phe Asp Leu Gly Gly Leu Tyr
675 680 685

Glu Ala Ile Glu Glu Cys Leu Ile Asn Asp Pro Trp Val Leu Leu Asn
690 695 700

Ala Ser Trp Phe Asn Ser Phe Leu Thr His Ala Leu Ser Leu Trp Gln
705 710 715 720

Cys Tyr Tyr Leu

<210> SEQ ID NO 10
<211> LENGTH: 2178
<212> TYPE: DNA
<213> ORGANISM: Influenza A virus

<400> SEQUENCE: 10
caaaatggaa gattttgtgc gacaatgctt caatccgatg attgtcgagc ttgcggaaaa 60
aacaatgaaa gagtatgggg aggacctgaa aatcgaaaca aacaaatttg cagcaatatg 120
cactcacttg gaagtatgct tcatgtattc agatttccac ttcatcaatg agcaaggcga 180
gtcaataatc gtagaacttg gtgatcctaa tgcacttttg aagcacagat ttgaaataat 240
cgagggaaga gatcgcacaa tggcctggac agtagtaaac agtatttgca acactacagg 300
ggctgagaaa ccaaagtttc taccagattt gtatgattac aaggaaaata gattcatcga 360
aattggagta acaaggagag aagttcacat atactatctg gaaaaggcca ataaaattaa 420
atctgagaaa acacacatcc acattttctc gttcactggg gaagaaatgg ccacaagggc 480
cgactacact ctcgatgaag aaagcagggc taggatcaaa accaggctat tcaccataag 540
acaagaaatg gccagcagag gcctctggga ttcctttcgt cagtccgaga gaggagaaga 600
gacaattgaa gaaaggtttg aaatcacagg aacaatgcgc aagcttgccg accaaagtct 660
cccgccgaac ttctccagcc ttgaaaattt tagagcctat gtggatggat tcgaaccgaa 720
cggctacatt gagggcaagc tgtctcaaat gtccaaagaa gtaaatgcta gaattgaacc 780
ttttttgaaa acaacaccac gaccacttag acttccgaat gggcctccct gttctcagcg 840
gtccaaattc ctgctgatgg atgccttaaa attaagcatt gaggacccaa gtcatgaagg 900
agagggaata ccgctatatg atgcaatcaa atgcatgaga acattctttg gatggaagga 960
acccaatgtt gttaaaccac acgaaaaggg aataaatcca aattatcttc tgtcatggaa 1020
gcaagtactg gcagaactgc aggacattga gaatgaggag aaaattccaa agactaaaaa 1080
tatgaaaaaa acaagtcagc taaagtgggc acttggtgag aacatggcac cagaaaaggt 1140
agactttgac gactgtaaag atgtaggtga tttgaagcaa tatgatagtg atgaaccaga 1200
attgaggtcg cttgcaagtt ggattcagaa tgagttcaac aaggcatgcg aactgacaga 1260
ttcaagctgg atagagcttg atgagattgg agaagatgtg gctccaattg aacacattgc 1320
aagcatgaga aggaattatt tcacatcaga ggtgtctcac tgcagagcca cagaatacat 1380
aatgaagggg gtgtacatca atactgcctt acttaatgca tcttgtgcag caatggatga 1440
tttccaatta attccaatga taagcaagtg tagaactaag gagggaaggc gaaagaccaa 1500
cttgtatggt ttcatcataa aaggaagatc ccacttaagg aatgacaccg acgtggtaaa 1560
ctttgtgagc atggagtttt ctctcactga cccaagactt gaaccacaca aatgggagaa 1620
gtactgtgtt cttgagatag gagatatgct tctaagaagt gccataggcc aggtttcaag 1680
gcccatgttc ttgtatgtga ggacaaatgg aacctcaaaa attaaaatga aatggggaat 1740

-continued

```
ggagatgagg cgttgtctcc tccagtcact tcaacaaatt gagagtatga ttgaagctga   1800

gtcctctgtc aaagagaaag acatgaccaa agagttcttt gagaacaaat cagaaacatg   1860

gcccattgga gagtctccca aaggagtgga ggaaagttcc attgggaagg tctgcaggac   1920

tttattagca aagtcggtat ttaacagctt gtatgcatct ccacaactag aaggattttc   1980

agctgaatca agaaaactgc ttcttatcgt tcaggctctt agggacaatc tggaacctgg   2040

gacctttgat cttgggggc tatatgaagc aattgaggag tgcctaatta atgatccctg   2100

ggttttgctt aatgcttctt ggttcaactc cttccttaca catgcattga gttagttgtg   2160

gcagtgctac tatttgct                                                 2178
```

<210> SEQ ID NO 11
<211> LENGTH: 269
<212> TYPE: PRT
<213> ORGANISM: Influenza A virus

<400> SEQUENCE: 11

```
Val Ser Ser Phe Gln Val Asp Cys Phe Leu Trp His Val Arg Lys Arg
1               5                   10                  15

Val Ala Asp Gln Glu Leu Gly Asp Ala Pro Phe Leu Asp Arg Leu Arg
            20                  25                  30

Arg Asp Gln Lys Ser Leu Arg Gly Arg Gly Ser Thr Leu Gly Leu Asp
        35                  40                  45

Ile Glu Thr Ala Thr Arg Ala Gly Lys Gln Ile Val Glu Arg Ile Leu
    50                  55                  60

Lys Glu Glu Ser Asp Glu Ala Leu Lys Met Thr Met Ala Ser Val Pro
65                  70                  75                  80

Ala Ser Arg Tyr Leu Thr Asp Met Thr Leu Glu Glu Met Ser Arg Glu
                85                  90                  95

Trp Ser Met Leu Ile Pro Lys Gln Lys Val Ala Gly Pro Leu Cys Ile
            100                 105                 110

Arg Met Asp Gln Ala Ile Met Asp Lys Asn Ile Ile Leu Lys Ala Asn
        115                 120                 125

Phe Ser Val Ile Phe Asp Arg Leu Glu Thr Leu Ile Leu Leu Arg Ala
    130                 135                 140

Phe Thr Glu Glu Gly Ala Ile Val Gly Glu Ile Ser Pro Leu Pro Ser
145                 150                 155                 160

Leu Pro Gly His Thr Ala Glu Asp Val Lys Asn Ala Val Gly Val Leu
                165                 170                 175

Ile Gly Gly Leu Glu Trp Asn Asp Asn Thr Val Arg Val Ser Glu Thr
            180                 185                 190

Leu Gln Arg Phe Ala Trp Arg Ser Ser Asn Glu Asn Gly Arg Pro Pro
        195                 200                 205

Leu Thr Pro Lys Gln Lys Arg Glu Met Ala Gly Thr Ile Arg Ser Glu
    210                 215                 220

Val Arg Asn Lys Met Val Asp Arg Ser Glu Thr Gln Thr Glu Gly Asn
225                 230                 235                 240

Arg Glu Phe Ala Asn Asn Ile Tyr Ala Ser Leu Thr Ser Ile Ala Ser
                245                 250                 255

Gly Ala Arg Asp Lys Asn Phe Leu Ile Ser Ala Tyr Leu
            260                 265
```

<210> SEQ ID NO 12
<211> LENGTH: 824
<212> TYPE: DNA

<213> ORGANISM: Influenza A virus

<400> SEQUENCE: 12

```
ctgtgtcaag ctttcaggta gattgctttc tttggcatgt ccgcaaacga gttgcagacc      60
aagaactagg tgatgcccca ttccttgatc ggcttcgccg agatcagaaa tccctaagag     120
gaaggggcag cactcttggt ctggacatcg agacagccac acgtgctgga aagcagatag     180
tggagcggat tctgaaagaa gaatccgatg aggcacttaa aatgaccatg gcctctgtac     240
ctgcgtcgcg ttacctaacc gacatgactc ttgaggaaat gtcaagggaa tggtccatgc     300
tcatacccaa gcagaaagtg gcaggccctc tttgtatcag aatggaccag gcgatcatgg     360
ataaaaacat catactgaaa gcgaacttca gtgtgatttt tgaccggctg gagactctaa     420
tattgctaag ggctttcacc gaagagggag caattgttgg cgaaatttca ccattgcctt     480
ctcttccagg acatactgct gaggatgtca aaaatgcagt tggagtcctc atcggaggac     540
ttgaatggaa tgataacaca gttcgagtct ctgaaactct acagagattc gcttggagaa     600
gcagtaatga gaatgggaga cctccactca ctccaaaaca gaaacgagaa atggcgggaa     660
caattaggtc agaagtttga agaaataaga tggttgattg aagaagtgag acacaaactg     720
aaggtaacag agaatagttt tgagcaaata acatttatgc aagccttaca tctattgctt     780
gaagtggagc aagagataag aactttctca tttcagctta ttta                      824
```

<210> SEQ ID NO 13
<211> LENGTH: 555
<212> TYPE: PRT
<213> ORGANISM: Influenza A virus

<400> SEQUENCE: 13

```
Phe Ala Ile Val Ser Leu Val Lys Ser Asp Gln Ile Cys Ile Gly Tyr
1               5                   10                  15

His Ala Asn Asn Ser Thr Glu Gln Val Asp Thr Ile Met Glu Lys Asn
            20                  25                  30

Val Thr Val Thr His Ala Gln Asp Ile Leu Glu Lys Thr His Asn Gly
        35                  40                  45

Lys Leu Cys Asp Leu Asp Gly Val Lys Pro Leu Ile Leu Arg Asp Cys
    50                  55                  60

Ser Val Ala Gly Trp Leu Leu Gly Asn Pro Met Cys Asp Glu Phe Ile
65                  70                  75                  80

Asn Val Pro Glu Trp Ser Tyr Ile Val Glu Lys Ala Asn Pro Val Asn
                85                  90                  95

Asp Leu Cys Tyr Pro Gly Asp Phe Asn Asp Tyr Glu Glu Leu Lys His
            100                 105                 110

Leu Leu Ser Arg Ile Asn His Phe Glu Lys Ile Gln Ile Ile Pro Lys
        115                 120                 125

Ser Ser Trp Ser Ser His Glu Ala Ser Leu Gly Val Ser Ser Ala Cys
    130                 135                 140

Pro Tyr Gln Gly Lys Ser Ser Phe Phe Arg Asn Val Val Trp Leu Ile
145                 150                 155                 160

Lys Lys Asn Ser Thr Tyr Pro Thr Ile Lys Arg Ser Tyr Asn Asn Thr
                165                 170                 175

Asn Gln Glu Asp Leu Leu Val Leu Trp Gly Ile His His Pro Asn Asp
            180                 185                 190

Ala Ala Glu Gln Thr Lys Leu Tyr Gln Asn Pro Thr Thr Tyr Ile Ser
        195                 200                 205

Val Gly Thr Ser Thr Leu Asn Gln Arg Leu Val Pro Arg Ile Ala Thr
```

-continued

```
    210                 215                 220

Arg Ser Lys Val Asn Gly Gln Ser Gly Arg Met Glu Phe Phe Trp Thr
225                 230                 235                 240

Ile Leu Lys Pro Asn Asp Ala Ile Asn Phe Glu Ser Asn Gly Asn Phe
                245                 250                 255

Ile Ala Pro Glu Tyr Ala Tyr Lys Ile Val Lys Lys Gly Asp Ser Thr
            260                 265                 270

Ile Met Lys Ser Glu Leu Glu Tyr Gly Asn Cys Asn Thr Lys Cys Gln
        275                 280                 285

Thr Pro Met Gly Ala Ile Asn Ser Ser Met Pro Phe His Asn Ile His
    290                 295                 300

Pro Leu Thr Ile Gly Glu Cys Pro Lys Tyr Val Lys Ser Asn Arg Leu
305                 310                 315                 320

Val Leu Ala Thr Gly Leu Arg Asn Ser Pro Gln Arg Glu Thr Arg Gly
                325                 330                 335

Leu Phe Gly Ala Ile Ala Gly Phe Ile Glu Gly Gly Trp Gln Gly Met
            340                 345                 350

Val Asp Gly Trp Tyr Gly Tyr His His Ser Asn Glu Gln Gly Ser Gly
        355                 360                 365

Tyr Ala Ala Asp Lys Glu Ser Thr Gln Lys Ala Ile Asp Gly Val Thr
    370                 375                 380

Asn Lys Val Asn Ser Ile Ile Asp Lys Met Asn Thr Gln Phe Glu Ala
385                 390                 395                 400

Val Gly Arg Glu Phe Asn Asn Leu Glu Arg Arg Ile Glu Asn Leu Asn
                405                 410                 415

Lys Lys Met Glu Asp Gly Phe Leu Asp Val Trp Thr Tyr Asn Ala Glu
            420                 425                 430

Leu Leu Val Leu Met Glu Asn Glu Arg Thr Leu Asp Phe His Asp Ser
        435                 440                 445

Asn Val Lys Asn Leu Tyr Asp Lys Val Arg Leu Gln Leu Arg Asp Asn
    450                 455                 460

Ala Lys Glu Leu Gly Asn Gly Cys Phe Glu Phe Tyr His Lys Cys Asp
465                 470                 475                 480

Asn Glu Cys Met Glu Ser Val Arg Asn Gly Thr Tyr Asp Tyr Pro Gln
                485                 490                 495

Tyr Ser Glu Glu Ala Arg Leu Lys Arg Glu Glu Ile Ser Gly Val Lys
            500                 505                 510

Leu Glu Ser Ile Gly Ile Tyr Gln Ile Leu Ser Ile Tyr Ser Thr Val
        515                 520                 525

Ala Ser Ser Leu Ala Leu Ala Ile Met Val Ala Gly Leu Ser Leu Trp
    530                 535                 540

Met Cys Ser Asn Gly Ser Leu Gln Cys Arg Ile
545                 550                 555
```

<210> SEQ ID NO 14
<211> LENGTH: 1666
<212> TYPE: DNA
<213> ORGANISM: Influenza A virus

<400> SEQUENCE: 14

```
ttttgcaata gtcagtcttg ttaaaagtga tcagatttgc attggttacc atgcaaacaa      60

ctcgacagag caggttgaca caataatgga aaagaacgtt actgttacac atgcccaaga     120

catactggaa aagacacaca atgggaagct ctgcgatcta gatggagtga agcctctaat     180

tttgagagat tgtagtgtag ctggatggct cctcggaaac ccaatgtgtg acgaattcat     240
```

caatgtgccg gaatggtctt acatagtgga gaaggccaat ccagtcaatg acctctgtta 300
cccaggggat ttcaatgact atgaagaatt gaaacaccta ttgagcagaa taaaccattt 360
tgagaaaatt cagatcatcc ccaaaagttc ttggtccagt catgaagcct cattgggggt 420
gagctcagca tgtccatacc agggaaagtc ctcctttttc agaaatgtgg tatggcttat 480
caaaaagaac agtacatacc caacaataaa gaggagctac aataatacca accaagaaga 540
tcttttggta ctgtggggga ttcaccatcc taatgatgcg gcagagcaga caaagctcta 600
tcaaaaccca accacctata tttccgttgg gacatcaaca ctaaaccaga gattggtacc 660
aagaatagct actagatcca aagtaaacgg gcaaagtgga aggatggagt tcttctggac 720
aattttaaaa ccgaatgatg caatcaactt cgagagtaat ggaaatttca ttgctccaga 780
atatgcatac aaaattgtca agaaagggga ctcaacaatt atgaaaagtg aattggaata 840
tggtaactgc aacaccaagt gtcaaactcc aatgggggcg ataaactcta gcatgccatt 900
ccacaatata caccctctca ccatcgggga atgccccaaa tatgtgaaat caaacagatt 960
agtccttgcg actgggctca gaaatagccc tcaacgagag acgcgaggat tatttggagc 1020
tatagcaggt tttatagagg gaggatggca gggaatggta gatggttggt atgggtacca 1080
ccatagcaac gagcagggga gtgggtacgc tgcagacaaa gaatccactc aaaaggcaat 1140
agatggagtc accaataagg tcaactcgat tattgacaaa atgaacactc agtttgaggc 1200
cgttggaagg gaatttaaca acttagaaag gagaatagag aatttaaaca agaagatgga 1260
agacgggttc ctagatgtct ggacttataa tgctgaactt ctagttctca tggaaaacga 1320
gagaactcta gactttcatg actcaaatgt caagaacctt tacgacaagg tccgactaca 1380
gcttagggat aatgcaaagg agctgggtaa cggttgtttc gagttctatc ataaatgtga 1440
taatgaatgt atggaaagtg taagaaacgg aacgtatgac tacccgcagt attcagaaga 1500
agcaagacta aaaagagagg aaataagtgg agtaaaattg gaatcaatag gaatttacca 1560
aatattgtca atttattcta cagtggcgag ctccctagca ctggcaatca tggtagctgg 1620
tctatcctta tggatgtgct ccaatgggtc gttacaatgc agaatt 1666

<210> SEQ ID NO 15
<211> LENGTH: 429
<212> TYPE: PRT
<213> ORGANISM: Influenza A virus
<220> FEATURE:
<221> NAME/KEY: misc_feature
<222> LOCATION: (429)..(429)
<223> OTHER INFORMATION: Xaa can be any naturally occurring amino acid

<400> SEQUENCE: 15

Thr Ile Gly Ser Ile Cys Met Val Thr Gly Ile Val Ser Leu Met Leu
1               5                   10                  15

Gln Ile Gly Asn Met Ile Ser Ile Trp Val Ser His Ser Ile His Thr
            20                  25                  30

Gly Asn Gln His Gln Ser Glu Pro Ile Ser Asn Thr Asn Leu Leu Thr
        35                  40                  45

Glu Lys Ala Val Ala Ser Val Lys Leu Ala Gly Asn Ser Ser Leu Cys
    50                  55                  60

Pro Ile Asn Gly Trp Ala Val Tyr Ser Lys Asp Asn Ser Ile Arg Ile
65                  70                  75                  80

Gly Ser Lys Gly Asp Val Phe Val Ile Arg Glu Pro Phe Ile Ser Cys
                85                  90                  95

Ser His Leu Glu Cys Arg Thr Phe Phe Leu Thr Gln Gly Ala Leu Leu

```
            100                 105                 110

Asn Asp Lys His Ser Asn Gly Thr Val Lys Asp Arg Ser Pro His Arg
        115                 120                 125

Thr Leu Met Ser Cys Pro Val Gly Glu Ala Pro Ser Pro Tyr Asn Ser
    130                 135                 140

Arg Phe Glu Ser Val Ala Trp Ser Ala Ser Ala Cys His Asp Gly Thr
145                 150                 155                 160

Ser Trp Leu Thr Ile Gly Ile Ser Gly Pro Asp Asn Gly Ala Val Ala
                165                 170                 175

Val Leu Lys Tyr Asn Gly Ile Ile Thr Asp Thr Ile Lys Ser Trp Arg
            180                 185                 190

Asn Asn Ile Leu Arg Thr Gln Glu Ser Glu Cys Ala Cys Val Asn Gly
        195                 200                 205

Ser Cys Phe Thr Val Met Thr Asp Gly Pro Ser Asn Gly Gln Ala Ser
    210                 215                 220

His Lys Ile Phe Lys Met Glu Lys Gly Lys Val Val Lys Ser Val Glu
225                 230                 235                 240

Leu Asp Ala Pro Asn Tyr His Tyr Glu Glu Cys Ser Cys Tyr Pro Asp
                245                 250                 255

Ala Gly Glu Ile Thr Cys Val Cys Arg Asp Asn Trp His Gly Ser Asn
            260                 265                 270

Arg Pro Trp Val Ser Phe Asn Gln Asn Leu Glu Tyr Gln Ile Gly Tyr
        275                 280                 285

Ile Cys Ser Gly Val Phe Gly Asp Asn Pro Arg Pro Asn Asp Gly Thr
    290                 295                 300

Gly Ser Cys Gly Pro Val Ser Ser Asn Gly Ala Gly Gly Val Lys Gly
305                 310                 315                 320

Phe Ser Phe Lys Tyr Gly Asn Gly Val Trp Ile Gly Arg Thr Lys Ser
                325                 330                 335

Thr Asn Ser Arg Ser Gly Phe Glu Met Ile Trp Asp Pro Asn Gly Trp
            340                 345                 350

Thr Glu Thr Asp Ser Ser Phe Ser Val Lys Gln Asp Ile Val Ala Ile
        355                 360                 365

Thr Asp Trp Ser Gly Tyr Ser Gly Ser Phe Val Gln His Pro Glu Leu
    370                 375                 380

Thr Gly Leu Asp Cys Ile Arg Pro Cys Phe Trp Val Glu Leu Ile Arg
385                 390                 395                 400

Gly Arg Pro Lys Glu Ser Thr Ile Trp Thr Ser Gly Ser Ser Ile Ser
                405                 410                 415

Phe Cys Gly Val Asn Ser Asp Thr Val Gly Trp Ser Xaa
            420                 425
```

<210> SEQ ID NO 16
<211> LENGTH: 1285
<212> TYPE: DNA
<213> ORGANISM: Influenza A virus

<400> SEQUENCE: 16

```
accatcggat caatctgtat ggtaactgga atagttagct taatgttaca aattgggaac      60

atgatctcaa tatgggtcag tcattcaatt cacacaggga atcaacacca atctgaacca     120

atcagcaata ctaatttgct tactgagaaa gctgtggctt cagtaaaatt agcgggcaat     180

tcatctcttt gccccattaa cggatgggct gtatacagta aggacaacag tataaggatc     240

ggttccaagg gggatgtgtt tgttataaga gagccgttca tctcatgctc ccacttggaa     300
```

-continued

```
tgcagaactt tctttttgac tcagggagcc ttgctgaatg acaagcactc caatgggact    360

gtcaaagaca gaagccctca cagaacatta atgagttgtc ctgtgggtga ggctccctcc    420

ccatataact caaggtttga gtctgttgct tggtcagcaa gtgcttgcca tgatggcacc    480

agttggttga caattggaat ttctggccca gacaatgggg cggtggctgt attgaaatac    540

aatggcataa taacagacac tatcaagagt tggaggaaca acatactgag aactcaagag    600

tctgaatgtg catgtgtaaa tggttcttgc tttactgtaa tgactgacgg accaagtaat    660

ggtcaggcat cacataagat cttcaaaatg gaaaaaggga aagtggttaa atcagtcgaa    720

ttggatgctc ctaattatca ctatgaggaa tgctcctgtt atcctgatgc cggcgaaatc    780

acatgtgtgt gcagggataa ttggcatggt tcaaatcggc catgggtatc tttcaatcaa    840

aatttggagt atcaaatagg atatatatgc agtggagttt tcggagacaa tccacgcccc    900

aatgatggaa caggtagttg tggtccggtg tcctctaacg gggcaggtgg ggtaaaaggg    960

ttttcattta aatacggcaa tggtgtctgg atcgggagaa ccaaaagcac taattccagg   1020

agcggcttcg aaatgatttg ggatccaaat gggtggactg aaacggacag cagcttttca   1080

gtgaaacaag atatcgtagc aataactgat tggtcaggat atagcgggag ttttgtccag   1140

catccagagc tgacaggact agattgcata agaccttgtt tctgggttga gttgatcaga   1200

gggcggccca aagagagcac aatttggact agtgggagca gcatatcttt ttgtggtgta   1260

aatagtgaca ctgtgggttg gtctt                                         1285
```